US012714757B2

(12) United States Patent
Hartnett et al.

(10) Patent No.: US 12,714,757 B2
(45) Date of Patent: Aug. 25, 2026

(54) METHODS AND COMPOSITIONS FOR THE EXPRESSION OF CONSTITUTIVELY ACTIVE RAP1A FROM A VMD2 PROMOTER

(71) Applicants: University of Utah Research Foundation, Salt Lake City, UT (US); University of Florida, Gainesville, FL (US)

(72) Inventors: Mary Elizabeth Hartnett, Salt Lake City, UT (US); Haibo Wang, Salt Lake City, UT (US); William Hauswirth, Knoxville, TN (US); Vince Chiodo, Gainesville, FL (US)

(73) Assignees: University of Utah Research Foundation, Salt Lake City, UT (US); University Of Flordia Research Foundation, Gainesville, FL (US)

( * ) Notice: Subject to any disclaimer, the term of this patent is extended or adjusted under 35 U.S.C. 154(b) by 1041 days.

(21) Appl. No.: 17/763,767

(22) PCT Filed: Sep. 25, 2020

(86) PCT No.: PCT/US2020/052744
§ 371 (c)(1),
(2) Date: Mar. 25, 2022

(87) PCT Pub. No.: WO2021/062169
PCT Pub. Date: Apr. 1, 2021

(65) Prior Publication Data

US 2022/0347318 A1 Nov. 3, 2022

Related U.S. Application Data

(60) Provisional application No. 62/905,880, filed on Sep. 25, 2019.

(51) Int. Cl.

| | |
|---|---|
| ***C12N 15/86*** | (2006.01) |
| ***A61K 9/00*** | (2006.01) |
| ***A61K 38/17*** | (2006.01) |
| ***A61K 38/46*** | (2006.01) |
| ***A61K 45/06*** | (2006.01) |
| ***A61K 48/00*** | (2006.01) |
| ***A61P 27/02*** | (2006.01) |
| ***C07K 14/705*** | (2006.01) |
| ***C12N 9/14*** | (2006.01) |

(52) U.S. Cl.
CPC ........ *A61K 48/0066* (2013.01); *A61K 9/0019* (2013.01); *A61K 9/0048* (2013.01); *A61K 38/177* (2013.01); *A61K 38/46* (2013.01); *A61K 45/06* (2013.01); *A61P 27/02* (2018.01); *C07K 14/705* (2013.01); *C12N 9/14* (2013.01); *C12N 15/86* (2013.01); *C12Y 306/05002* (2013.01); *C12N 2780/00043* (2013.01); *C12N 2780/00071* (2013.01)

(58) Field of Classification Search
CPC ...... C12N 15/86; A61K 48/00; A61K 48/005; A61K 48/0058; A61K 48/0075; A61P 27/02
See application file for complete search history.

(56) References Cited

U.S. PATENT DOCUMENTS

| | | | | |
|---|---|---|---|---|
| 9,163,259 | B2 * | 10/2015 | Choi | A61P 27/02 |
| 2004/0022766 | A1 * | 2/2004 | Acland | C12N 15/86 424/93.2 |
| 2011/0318738 | A1 | 12/2011 | Jones et al. | |
| 2014/0196176 | A1 * | 7/2014 | Heintz | C12N 15/1003 536/25.4 |
| 2015/0111955 | A1 * | 4/2015 | High | C12N 15/86 435/456 |
| 2018/0080046 | A1 * | 3/2018 | Choi | C12N 7/00 |

FOREIGN PATENT DOCUMENTS

WO WO 2020/047476 A1 3/2020

OTHER PUBLICATIONS

Guziewicz et al, Recombinant AAV-Mediated BEST1 Transfer to the Retinal Pigment Epithelium: Analysis of Serotype-Dependent Retinal Effects, PLoS One 8(10): 11 pages, e75666, 2013.*
www.calculator.net/exponent-calculator.html; last visited Mar. 17, 2025.*
Moreira et al, Hot spots—A review of the protein-protein interface determinant amino-acid residues, Proteins 68: 803-812, 2007.*
Ng et al, Predicting the Effects of Amino Acid Substitutions on Protein Function, Annual Review Genomics Human Genetics 7: 61-80, 2006.*
Kingdoms of Life, waynesword.palomar.edu/trfeb98.htm, last visited Apr. 8, 2021.*
Mammal, en.wikipedia.org/wiki/Mammal, last visited Aug. 31, 2022.*
Fumoto et al, Targeted Gene Delivery: Importance of Administration Routes, INTECH, Novel Gene Therapy Approaches, p. 3-31; editors Wei and Good, publisher Books on Demand, 2013.*
Daya et al, Gene Therapy Using Adeno-Associated Virus Vectors, Clin. Microbiol. Rev. 21(4): 583-593, 2008.*
Huang et al, Genetic Manipulation of Brown Fat via Oral Administration of an Engineered Recombinant Adeno-associated Viral Serotype Vector, Molecular Therapy 24(6): 1062-1069, 2016.*

(Continued)

*Primary Examiner* — Kevin K Hill
(74) *Attorney, Agent, or Firm* — Ballard Spahr LLP

(57) ABSTRACT

Disclosed are nucleic acid constructs comprising a nucleic acid sequence encoding a vitelliform macular dystrophy-2 (VMD2) promoter operably linked to a nucleic acid sequence encoding Rap1a. Disclosed are vectors comprising the nucleic acid constructs disclosed herein. Disclosed are compositions comprising the disclosed nucleic acid constructs or vectors. Also disclosed are methods of treating a subject having age-related macular degeneration comprising administering one or more of the disclosed nucleic acid constructs, vectors, or compositions to a subject in need thereof.

14 Claims, 7 Drawing Sheets

Specification includes a Sequence Listing.

(56) References Cited

OTHER PUBLICATIONS

Tian et al, Aerosol Inhalation-mediated Delivery of an Adeno-associated Virus 5-expressed Antagonistic Interleukin-4 Mutant Ameliorates Experimental Murine Asthma, Archives of Medical Research 50: 384-392, 2019.*

Ghoraba et al, Ocular Gene Therapy: A Literature Review with Special Focus on Immune and Inflammatory Responses, Clinical Opthalmology 16: 1753-1771, 2022.*

Mingozzi and High, Immune responses to AAV vectors: overcoming barriers to successful gene therapy, Blood 122(1): 23-36, 2013.*

Kattenhorn et al, Adeno-Associated Virus Gene Therapy for Liver Disease, Human Gene Therapy 27(12): 947-961, Nov. 28, 2016.*

Ferdowsian et al, Primates in Medical Research: A Matter of Convenience, not Sound Science, The Hastings Center, www.thehastingscenter.org/primates-in-medical-research-convenience-not-sound-science/; Jul. 8, 2022.*

Perrin, Make mouse studies work, Nature (507): 423-425, 2014.*

Greenberg, Gene Therapy for heart failure, Trends in Cardiovascular Medicine 27: 216-222, 2017.*

Maguire et al, Viral vectors for gene delivery to the inner ear, Hearing Research 394: e107927, 13 pages, doi.org/10.1016/j.heares.2020.107927, 2020.*

Tobias, Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023.*

Wang et al, Retinal pigment epithelial cell expression of active Rap1a by scAAV2 inhibits choroidal neovascularization, Molecular Therapy-Methods & Clinical Development 3: e16056, 11 pages, doi:10.1038/mtm.2016.56; available online Aug. 24, 2016.*

Daniel et al, ATGme: Open-source web application for rare codon identification and custom DNA sequence optimization, BMC Bioinformatics 16: 303, 6 pages, doi.10.1186/s12859-015-0743-5; 2015.*

GenBank A32342, human Rap1a; 2001.*

Ghazi, Nicola G., et al., "Treatment of retinitis pigmentosa due to MERTK mutations by ocular subretinal injection of adeno-associated virus gene vector: results of a phase I trial," Human Genetics, Springer Berlin Heidelberg, Berlin/Heidelberg, 135(3): 327-343 (2016).

Wang, Yuhong, et al., "Cell-Specific Promoters Enable Lipid-Based Nanoparticles to Deliver Genes to Specific Cells of the Retina In Vivo," Theranostics, 6,(10): 1514-1527 (2016).

U.S. Appl. No. 62/905,880, filed Sep. 25, 2019, Hartnett (University of Utah Research Foundation).

PCT, PCT/US2020/052744 (WO 2021/062169), Sep. 25, 2020 (Apr. 1, 2021), Hartnett (University of Utah Research Foundation).

Ablonczy, Z., Dahrouj, M. & Marneros, A. G., "Progressive dysfunction of the retinal pigment epithelium and retina due to increased VEGF-A levels." *FASEB J*, doi:10.1096/fj.13-248021 (2014).

Ahmed, C. M. et al., "Repurposing an orally available drug for the treatment of geographic atrophy." *Molecular vision* 22, 294-310 (2016).

Ardeljan, D. & Chan, C. C., "Aging is not a disease: distinguishing age-related macular degeneration from aging," *Prog Retin Eye Res* 37, 68-89, doi:10.1016/j.preteyeres.2013.07.003 (2013).

Bhutto, I. & Lutty, G., "Understanding age-related macular degeneration (AMD): relationships between the photoreceptor/retinal pigment epithelium/Bruch's membrane/choriocapillaris complex," *Mol Aspects Med* 33, 295-317, doi:10.1016/j.mam.2012.04.005 (2012).

Blasiak, J., Petrovski, G., Vereb, Z., Facsko, A. & Kaarniranta, K., "Oxidative stress, hypoxia, and autophagy in the neovascular processes of age-related macular degeneration," *Biomed Res Int* 2014, 768026, doi:10.1155/2014/768026 (2014).

Ehlken, C. et al., "Switch of anti-VEGF agents is an option for nonresponders in the treatment of AMD," *Eye* (London, England) 28, 538-545, doi:10.1038/eye.2014.64 (2014).

Ford, K. M., Saint-Geniez, M., Walshe, T., Zahr, A. & D'Amore, P. A., "Expression and Role of VEGF in the Adult Retinal Pigment Epithelium," *Investigative ophthalmology & visual science* 52, 9478-9487 (2011).

Fritsche, L. G. et al., "Age-related macular degeneration: genetics and biology coming together," *Annu Rev Genomics Hum Genet* 15, 151-171, doi:10.1146/annurev-genom-090413-025610 (2014).

He, L., Marioutina, M., Dunaief, J. L. & Marneros, A. G., "Age- and gene-dosage-dependent cre-induced abnormalities in the retinal pigment epithelium," *Am J Pathol* 184, 1660-1667, doi:10.1016/j.ajpath.2014.02.007 (2014).

Karakosta, A. et al., "Choice of analytic approach for eye-specific outcomes: one eye or two?" *American journal of ophthalmology* 153, 571-579.e571, doi:10.1016/j.ajo.2011.08.032 (2012).

Keeling, E., Lotery, A. J., Tumbarello, D. A. & Ratnayaka, J. A., "Impaired Cargo Clearance in the Retinal Pigment Epithelium (RPE) Underlies Irreversible Blinding Diseases". *Cells* 7, doi:10.3390/cells7020016 (2018).

Lancon, A., Frazzi, R. & Latruffe, N., "Anti-Oxidant, Anti-Inflammatory and Anti-Angiogenic Properties of Resveratrol in Ocular Diseases". *Molecules* 21, 304, doi:10.3390/molecules21030304 (2016).

Laredj, L. N. & Beard, P., "Adeno-Associated Virus Activates an Innate Immune Response in Normal Human Cells but Not in Osteosarcoma Cells," *Journal of Virology* 85, 13133-13143, doi:10.1128/jvi.05407-11 (2011).

Markomichelakis, N. N., Theodossiadis, P. G. & Sfikakis, P. P., "Regression of neovascular age-related macular degeneration following infliximab therapy," *American journal of ophthalmology* 139, 537-540, doi:10.1016/j.ajo.2004.09.058 (2005).

Mingozzi, F. & High, K. A., "Immune responses to AAV vectors: overcoming barriers to successful gene therapy," *Blood* 122, 23-36, doi:10.1182/blood-2013-01-306647 (2013).

Moshfegh, Y. et al., "BESTROPHIN1 mutations cause defective chloride conductance in patient stem cell-derived RPE," *Human molecular genetics* 25, 2672-2680, doi:10.1093/hmg/ddw126 (2016).

Murdoch, I. E., Morris, S. S. & Cousens, S. N., "People and eyes: statistical approaches in ophthalmology," *The British journal of ophthalmology* 82, 971-973, doi:10.1136/bjo.82.8.971 (1998).

Naso, M. F., Tomkowicz, B., Perry, W. L., 3rd & Strohl, W. R., "Adeno-Associated Virus (AAV) as a Vector for Gene Therapy," *BioDrugs : clinical immunotherapeutics, biopharmaceuticals and gene therapy* 31, 317-334, doi:10.1007/s40259-017-0234-5 (2017).

Oslowski, C. M. & Urano, F., "Measuring ER stress and the unfolded protein response using mammalian tissue culture system," *Methods in enzymology* 490, 71-92, doi:10.1016/B978-0-12-385114-7.00004-0 (2011).

Sennlaub, F. et al., "CCR2<sup>+</sup> monocytes infiltrate atrophic lesions in age-related macular disease and mediate photoreceptor degeneration in experimental subretinal inflammation in <em>Cx3cr1 </em> deficient mice," *EMBO Molecular Medicine* 5, 1775-1793, doi:10.1002/emmm.201302692 (2013).

Sobrin, L. & Seddon, J. M., "Nature and nurture—genes and environment—predict onset and progression of macular degeneration," *Prog Retin Eye Res* 40, 1-15, doi:10.1016/j.preteyeres.2013.12.004 (2014).

Sparrow, J. R., Ueda, K. & Zhou, J., "Complement dysregulation in AMD: RPE-Bruch's membrane-choroid," *Mol Aspects Med* 33, 436-445, doi:10.1016/j.mam.2012.03.007 (2012).

Telander, D. G., "Inflammation and age-related macular degeneration (AMD)," *Semin Ophthalmol* 26, 192-197, doi:10.3109/08820538.2011.570849 (2011).

Theodossiadis, P. G., Liarakos, V. S., Sfikakis, P. P., Vergados, I. A. & Theodossiadis, G. P., "Intravitreal administration of the anti-tumor necrosis factor agent infliximab for neovascular age-related macular degeneration," *American journal of ophthalmology* 147, 825-830, 830 e821, doi:10.1016/j.ajo.2008.12.004 (2009).

Veloso, C. E., de Almeida, L. N., Recchia, F. M., Pelayes, D. & Nehemy, M. B., "VEGF gene polymorphism and response to intravitreal ranibizumab in neovascular age-related macular degeneration," *Ophthalmic Res* 51, 1-8, doi:10.1159/000354328 (2014).

(56) References Cited

OTHER PUBLICATIONS

Wang, H. et al., "Activation of Rap1 inhibits NADPH oxidase-dependent ROS generation in retinal pigment epithelium and reduces choroidal neovascularization," *FASEB J*, doi:10.1096/fj.13-240028 (2013).

Wang, H., Fotheringham, L., Wittchen, E. S. & Hartnett, M. E., "Rap1 GTPase Inhibits Tumor Necrosis Factor-alpha-Induced Choroidal Endothelial Migration via NADPH Oxidase- and NF-kappaB-Dependent Activation of Rac1," *Am J Pathol* 185, 3316-3325, doi:10.1016/j.ajpath.2015.08.017 (2015).

Wang, H. & Hartnett, M. E., "Regulation of signaling events involved in the pathophysiology of neovascular AMD," *Molecular vision* 22, 189-202 (2016).

Wang, H. et al., "Retinal pigment epithelial cell expression of active Rap 1a by scAAV2 inhibits choroidal neovascularization," *Mol Ther Methods Clin Dev* 3, 16056, doi:10.1038/mtm.2016.56 (2016).

Wang, H., Han, X., Wittchen, E. S. & Hartnett, M. E., "TNF-alpha mediates choroidal neovascularization by upregulating VEGF expression in RPE through ROS-dependent beta-catenin activation," *Molecular vision* 22, 116-128 (2016).

Wang et al., "Optimal Inhibition of Choroidal Neovascularization by ScAAV2 with VMD2 Promoter-Driven Active Rap1a in the RPE," Scientific Reports, Oct. 31, 2019 (Oct. 31, 2019), vol. 9, No. 6732, pp. 1-11.

Wang, H., et al., "VMD2 Promoter-mediated Gene Therapy Optimizes Active Rap1a Expression in the Retinal Pigment Epithelium of Wild Type Mice | IOVS | ARVO Journals," Investigative Ophthalmology & Visual Science, vol. 60(1) Jul. 2019, p. 1925, XP093082395.

Wittchen, E. S. et al., "Rap1 GTPase Activation and Barrier Enhancement in RPE Inhibits Choroidal Neovascularization In Vivo," *PloS one* 8, e73070, doi:10.1371/journal.pone.0073070 (2013).

International Search Report and Written Opinion mailed Feb. 22, 2021 for International Application PCT/US2020/052744 filed Sep. 25, 2020 (8 pages).

International Preliminary Report on Patentability issued Mar. 15, 2022 for International Application PCT/US2020/052744 filed Sep. 25, 2020 (5 pages).

European Search Report mailed Oct. 4, 2023 in EP Application No. 20868555.2, filed Apr. 1, 2021, 8 Pages.

NCBI Reference Sequence: NP 001005765; National Center for Biotechnology Information (NCBI); https://www.ncbi.nim.nih.gov/protein/54114993; Feb. 16, 2019.

Guziewicz, K., et al., "Recombinant AAV-Mediated BEST1 Transfer to the Retinal Pigment Epithelium: Analysis of Serotype-Dependent Retinal Effects," PLOS One, 8(10): e75666, 11 Pages, (2013).

* cited by examiner

SEQUENCE LISTING

<160> NUMBER OF SEQ ID NOS: 4

<210> SEQ ID NO 1
<211> LENGTH: 624
<212> TYPE: DNA
<213> ORGANISM: Homo sapiens

<400> SEQUENCE: 1
caattctgtc attttactag ggtgatgaaa ttcccaagca acaccatcct tttcagataa 60
gggcactgag gctgagagag gagctgaaac ctacccggcg tcaccacaca caggtggcaa 120
ggctgggacc agaaaccagg actgttgact gcagcccggt attcattctt tccatagccc 180
acagggctgt caaagacccc agggcctagt cagaggctcc tccttcctgg agagttcctg 240
gcacagaagt tgaagctcag cacagccccc taaccccaa ctctctctgc aaggcctcag 300
gggtcagaac actggtggag cagatccttt agcctctgga ttttagggcc atggtagagg 360
gggtgttgcc ctaaattcca gccctggtct cagcccaaca ccctccaaga agaaattaga 420
ggggccatgg ccaggctgtg ctagccgttg cttctgagca gattacaaga agggaccaag 480
acaaggactc ctttgtggag gtcctggctt agggagtcaa gtgacggcgg ctcagcactc 540
acgtgggcag tgccagcctc taagagtggg caggggcact ggccacagag tcccagggag 600
tcccaccagc ctagtcgcca gacc 624

<210> SEQ ID NO 2
<211> LENGTH: 555
<212> TYPE: DNA
<213> ORGANISM: Homo sapiens

<400> SEQUENCE: 2
atgcgggaat acaagcttgt ggtgctgggc tctggaggcg tgggaaagag tgcgttaacc 60
gtccagtttg tgcagggcat ctttgtggag aagtatgatc ccactataga ggactcctac 120
cggaaacagg tggaggtcga ctgtcagcaa tgtatgctgg agatcttaga cactgcaggt 180
acagaagaat ttactgccat gcgggacctg tacatgaaga acgggcaggg cttcgctctg 240
gtatattcca tcaccgctca gtcaaccttt aacgaccttc aggatcttcg cgagcagatc 300
ctacgcgtga aagatacaga ggacgtccca atgatactag tgggcaacaa gtgtgacctg 360
gaggatgaac gggttgtggg caaggagcag ggtcagaacc tggccaggca gtggtgcaac 420

-continued tgtgcctttc tggaatctag cgccaagtcc aagatcaacg taaacgagat cttctacgac 480
ctagtacgtc agattaaccg gaagacacct gtggagaaga agaaacctaa gaagaaatcc 540
tgcctgcttc tctga 555

<210> SEQ ID NO 3
<211> LENGTH: 554
<212> TYPE: DNA
<213> ORGANISM: Homo sapiens

<400> SEQUENCE: 3
atgcgtgagt acaagctagt ggtccttggt tcaggaggcg ttgggaagtc tgctctgaca 60
gttcagtttg tcagggaatt tttgttgaaa aatatgaccc aacgatagaa gattcctaca 120
gaaagcaagt tgaagtcgat tgccaacagt gtatgctcga aatcctggat actgcaggga 180
cagagcaatt tacagcaatg agggatttgt atatgaagaa cggccaaggt tttgcactag 240
tatattctat tacagctcag tccacgttta acgacttaca ggacctgagg gaacagattt 300
tacgggttaa ggacacggaa gatgttccaa tgattttggt tggcaataaa tgtgacctgg 360
aagatgagcg agtagttggc aaagagcagg gccagaattt agcaagacag tggtgtaact 420
gtgccttttt agaatcttct gcaaagtcaa agatcaatgt taatgagata ttttatgacc 480
tggtcagaca gataaatagg aaaacaccag tggaaaagaa gaagcctaaa aagaaatcat 540
gtctgctgct ctag 554

<210> SEQ ID NO 4
<211> LENGTH: 184
<212> TYPE: PRT
<213> ORGANISM: Homo sapiens

<400> SEQUENCE: 4

Met Arg Glu Tyr Lys Leu Val Val Leu Gly Ser Gly Gly Val Gly Lys
1 5 10 15

Ser Ala Leu Thr Val Gln Phe Val Gln Gly Ile Phe Val Glu Lys Tyr
20 25 30

Asp Pro Thr Ile Glu Asp Ser Tyr Arg Lys Gln Val Glu Val Asp Cys
35 40 45

Gln Gln Cys Met Leu Glu Ile Leu Asp Thr Ala Gly Thr Glu Glu Phe
50 55 60

Thr Ala Met Arg Asp Leu Tyr Met Lys Asn Gly Gln Gly Phe Ala Leu
65 70 75 80

Val Tyr Ser Ile Thr Ala Gln Ser Thr Phe Asn Asp Leu Gln Asp Leu
85 90 95

Arg Glu Gln Ile Leu Arg Val Lys Asp Thr Glu Asp Val Pro Met Ile
100 105 110

Leu Val Gly Asn Lys Cys Asp Leu Glu Asp Glu Arg Val Val Gly Lys
115 120 125

Glu Gln Gly Gln Asn Leu Ala Arg Gln Trp Cys Asn Cys Ala Phe Leu
130 135 140

Glu Ser Ser Ala Lys Ser Lys Ile Asn Val Asn Glu Ile Phe Tyr Asp
145 150 155 160

Leu Val Arg Gln Ile Asn Arg Lys Thr Pro Val Glu Lys Lys Lys Pro
165 170 175

Lys Lys Lys Ser Cys Leu Leu Leu
180

METHODS AND COMPOSITIONS FOR THE EXPRESSION OF CONSTITUTIVELY ACTIVE RAP1A FROM A VMD2 PROMOTER

CROSS-REFERENCE TO RELATED APPLICATION

This application is a national stage application under 35 U.S.C. § 371 of International Application No. PCT/US2020/052744, filed on Sep. 25, 2020, which claims the benefit of U.S. Provisional Patent Application No. 62/905,880, filed on Sep. 25, 2019. The content of these earlier filed applications is hereby incorporated herein by reference in their entirety.

STATEMENT REGARDING FEDERALLY SPONSORED RESEARCH

This invention was made with government support under grants no. EY017011 and EY015130 awarded by the National Institutes of Health. The government has certain rights in the invention.

REFERENCE TO SEQUENCE LISTING

The Sequence Listing submitted Mar. 25, 2022 as a text file named "21101_0402U2_Sequence_Listing.txt," created on Mar. 25, 2022, and having a size of 4,633 bytes is hereby incorporated by reference pursuant to 37 C.F.R. § 1.52(e)(5).

BACKGROUND

Age-related macular degeneration (AMD) remains a leading cause of legal blindness in the elderly worldwide. Evidence suggests that dysfunction of the retinal pigment epithelium (RPE) precedes both neovascular and atrophic forms of AMD and may be important in the pathogenesis of these end-stage forms of AMD. The RPE is a monolayer of polarized cells that is critically important in retinal homeostasis. The RPE maintains the outer blood-retinal barrier while it regulates nutrient and oxygen delivery to the outer retina and removal of metabolic waste from the photoreceptors. The RPE also produces growth factors at a physiologic level that support the retina and choriocapillaris. With aging and increasing pathologic stresses, the RPE can lose the efficiency of these functions. As a result, accumulation of debris within Bruch's membrane appears as drusen beneath the RPE. As dysfunction progresses, the barrier integrity of the RPE is compromised and stressed RPE releases growth factors at a pathologic level that lead to advanced AMD. Therefore, strategies to maintain or restore functions of the RPE might be potential targets for AMD therapy.

Thus, disclosed herein compositions for and methods of treating a subject having age-related macular degeneration.

BRIEF SUMMARY

Disclosed are nucleic acid constructs comprising a nucleic acid sequence encoding a vitelliform macular dystrophy-2 (VMD2) promoter operably linked to a nucleic acid sequence encoding active Rap1a Disclosed are vectors comprising the nucleic acid constructs disclosed herein.

Disclosed are compositions comprising the nucleic acid constructs or vectors disclosed herein.

Disclosed are recombinant cells comprising one or more of the nucleic acid constructs or vectors disclosed herein.

Disclosed are methods of treating a subject having age-related macular degeneration comprising administering one or more of the nucleic acid constructs, vectors, or compositions to a subject in need thereof.

Disclosed are methods of inhibiting choroidal neovascularization (CNV) comprising administering to a subject one or more of the nucleic acid constructs, vectors, or compositions disclosed herein.

Disclosed are methods of reducing inflammatory signaling in choroid tissue comprising administering to a subject one or more of the nucleic acid constructs, vectors, or compositions disclosed herein.

Disclosed are methods of reducing VEGF expression in choroid tissue comprising administering to a subject one or more of the nucleic acid constructs, vectors, or compositions disclosed herein.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figures 1A, 1B:
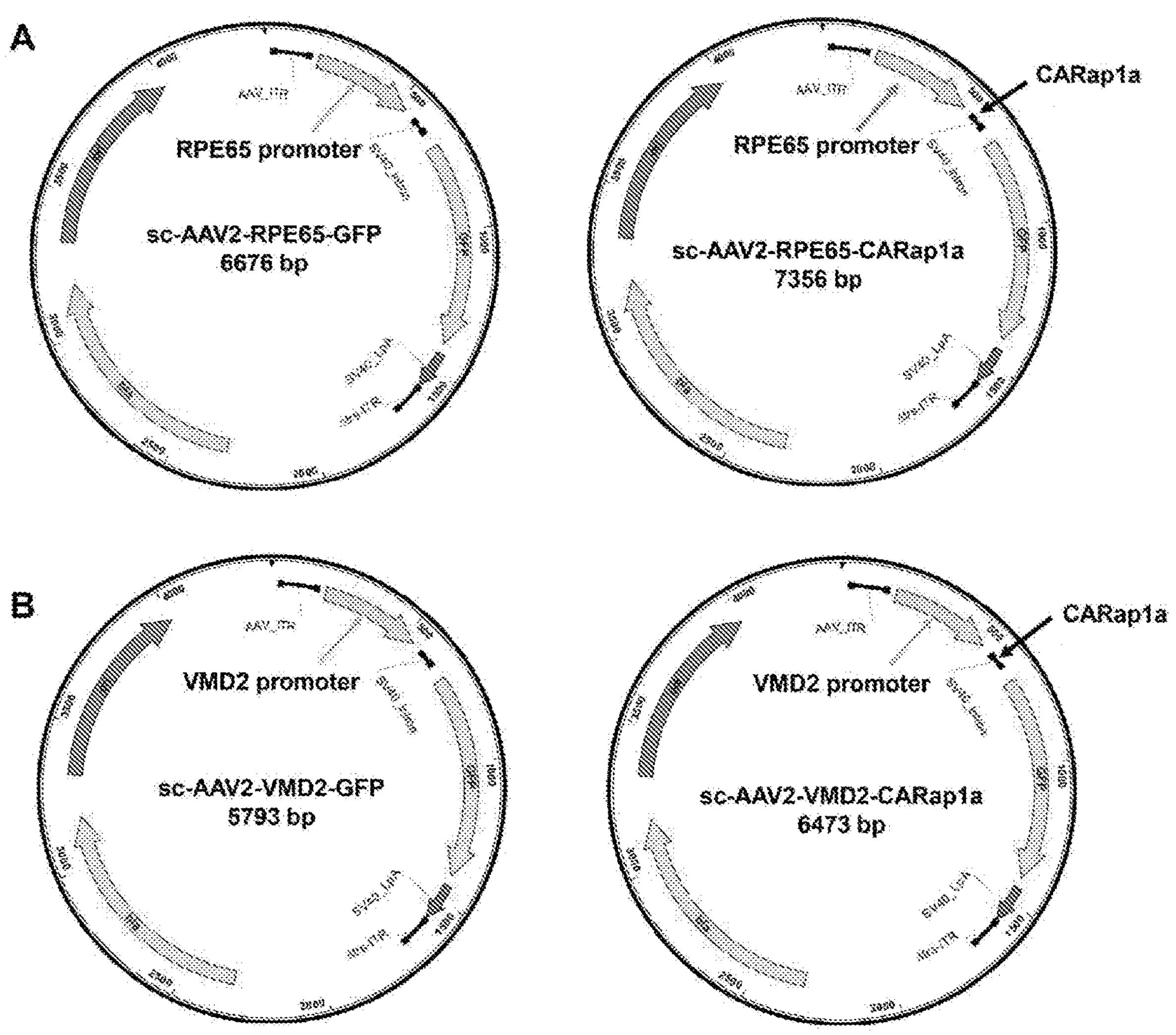
FIGS. 1A and 1B show diagrams of self-complementary adeno-associated virus 2 (sc-AAV2) vectors to deliver constitutively active Rap1a (CARap1a) or only GFP driven by (A) an RPE65 promoter (sc-AAV2-RPE65-CARap1a and sc-AAV2-RPE65-GFP) or (B) a VMD2 promoter (sc-AAV2-VMD2-CARap1a and sc-AAV2-VMD2-GFP).

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a nucleic acid sequence" includes a plurality of such nucleic acid sequences, reference to "the vector" is a reference to one or more vectors and equivalents thereof known to those skilled in the art, and so forth.

The expression "operationally linked" means that the promoter sequence is positioned relative to the coding sequence of the gene of interest such that transcription is able to start. This means that the promoter is positioned upstream of the coding sequence, at a distance enabling the expression of the coding sequence.

The term "percent (%) homology" is used interchangeably herein with the term "percent (%) identity" and refers to the level of nucleic acid or amino acid sequence identity when aligned with a wild type sequence using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for anyone of the inventive polypeptides, as described herein. Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997. Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62matrix. (See, e.g., Altschul, S. F., et al., Nucleic Acids Res. 25:3389-3402, 1997.) A preferred alignment of selected sequences in order to determine"% identity" between two or more sequences, is performed using for example, the CLUSTAL-W program in Mac Vector version 13.0.7, operated with default parameters, including an open gap penalty of 10.0, an extended gap penalty of 0.1, and a BLOSUM 30 similarity matrix.

As used herein, the term "wild-type" refers to a gene or gene product which has the characteristics of that gene or gene product when isolated from a naturally-occurring source.

The terms "variant" and "mutant" are used interchangeably herein. As used herein, the term "mutant" refers to a modified nucleic acid or protein which displays the same characteristics when compared to a reference nucleic acid or protein sequence. A variant can be at least 65, 70, 75, 80, 85, 90, 95, or 99 percent homologues to a reference sequence. In some aspects, a reference sequence can be a CARap1a nucleic acid sequence or an active Rap1a protein sequence. Variants can also include nucleotide sequences that are substantially similar to sequences of miRNA disclosed herein. A "variant" can mean a difference in some way from the reference sequence other than just a simple deletion of an N- and/or C-terminal nucleotide. Variants can also or alternatively include at least one substitution and/or at least one addition, there may also be at least one deletion. Alternatively or in addition, variants can comprise modifications, such as non-natural residues at one or more positions with respect to a reference nucleic acid or protein.

Substitutions, deletions, insertions or any combination thereof may be used to arrive at a final derivative or variant. Generally, these changes are done on a few nucleotides to minimize the alteration of the molecule. However, larger changes may be tolerated in certain circumstances.

Generally, the nucleotide identity between individual variant sequences can be at least 90%, 91%, 92%, 93%, 94%, 95%, 96%, 97%, 98%, 99%, or 100%. Thus, a "variant sequence" can be one with the specified identity to the parent or reference sequence (e.g. wild-type sequence) of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent sequence. For example, a "variant sequence" can be a sequence that contains 1, 2, or 3 4 nucleotide base changes as compared to the parent or reference sequence of the invention, and shares or improves biological function, specificity and/or activity of the parent sequence. Thus, a "variant sequence" can be one with the specified identity to the parent sequence of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent sequence. The variant sequence can also share at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of a reference sequence (e.g. wild-type sequence, a CARap1a nucleic acid sequence or a active Rap1a protein sequence).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By an "effective amount" of a composition as provided herein is meant a sufficient amount of the composition to provide the desired effect. The exact amount required will vary from subject to subject, depending on the species, age, and general condition of the subject, the severity of disease (or underlying genetic defect) that is being treated, the particular composition used, its mode of administration, and the like. Thus, it is not possible to specify an exact "effective amount." However, an appropriate "effective amount" may be determined by one of ordinary skill in the art using only routine experimentation.

By "treat" is meant to administer a peptide, nucleic acid, vector, or composition of the invention to a subject, such as a human or other mammal (for example, an animal model), that has an increased susceptibility for developing age-related macular degeneration, or that has age-related macular degeneration, in order to prevent or delay a worsening of the effects of the disease or condition, or to partially or fully reverse the effects of the disease.

By "prevent" is meant to minimize the chance that a subject who has an increased susceptibility for developing age-related macular degeneration.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Nucleic Acids

Disclosed are nucleic acid constructs comprising a nucleic acid sequence encoding a vitelliform macular dystrophy-2 (VMD2) promoter operably linked to a nucleic acid sequence encoding Rap1a. Also disclosed are nucleic acid constructs comprising a nucleic acid sequence encoding a vitelliform macular dystrophy-2 (VMD2) promoter operably linked to a constitutively active Rap1a nucleic acid sequence. Also disclosed are nucleic acid constructs comprising a nucleic acid sequence encoding a vitelliform macular dystrophy-2 (VMD2) promoter operably linked to a nucleic acid sequence encoding active Rap1a.

In some aspects, the VMD2 promoter is human VMD2 promoter. In some aspects, the human VMD2 promoter can be (SEQ ID NO: 1)

CAATTCTGTCATTTTACTAGGGTGATGAAATTCCCAAGCAACACCATCCT

TTTCAGATAAGGGCACTGAGGCTGAGAGAGGAGCTGAAACCTACCCGGCG

TCACCACACACAGGTGGCAAGGCTGGGACCAGAAACCAGGACTGTTGACT

GCAGCCCGGTATTCATTCTTTCCATAGCCCACAGGGCTGTCAAAGACCCC

AGGGCCTAGTCAGAGGCTCCTCCTTCCTGGAGAGTTCCTGGCACAGAAGT

TGAAGCTCAGCACAGCCCCCTAACCCCCAACTCTCTCTGCAAGGCCTCAG

GGGTCAGAACACTGGTGGAGCAGATCCTTTAGCCTCTGGATTTTAGGGCC

ATGGTAGAGGGGGTGTTGCCCTAAATTCCAGCCCTGGTCTCAGCCCAACA

CCCTCCAAGAAGAAATTAGAGGGGCCATGGCCAGGCTGTGCTAGCCGTTG

CTTCTGAGCAGATTACAAGAAGGGACCAAGACAAGGACTCCTTTGTGGAG

GTCCTGGCTTAGGGAGTCAAGTGACGGCGGCTCAGCACTCACGTGGGCAG

TGCCAGCCTCTAAGAGTGGGCAGGGGCACTGGCCACAGAGTCCCAGGGAG

TCCCACCAGCCTAGTCGCCAGACC.

In some aspects, the VMD2 promoter is a variant of SEQ ID NO:1. In some aspects, the VMD2 promoter is 65, 70, 75, 80, 85, 90, 95, or 99 percent homologous to SEQ ID NO:1.

In some aspects, the encoded Rap1a protein is active Rap1a protein. In some aspects, the active Rap1a protein is encoded by a constitutively active Rap1a (CARap1a) nucleic acid sequence. As used herein, the terms "CARap1a", "constitutively active Rap1a" and "constitutively active Rap1a nucleic acid" are used interchangeably. In other words, a constitutively active Rap1a nucleic acid sequence can encode an active Rap1a protein. As used herein, the terms "active Rap1a protein" and "active Rap1a" are used interchangeably. In some aspects, the active Rap1a protein is human Rap1a protein. In some aspects, the constitutively active Rap1a nucleic acid sequence that encodes human active Rap1a can be (SEQ ID NO: 2)

ATGCGGGAATACAAGCTTGTGGTGCTGGGCTCTGGAGGCGTGGGAAAGAG

TGCGTTAACCGTCCAGTTTGTGCAGGGCATCTTTGTGGAGAAGTATGATC

-continued

CCACTATAGAGGACTCCTACCGGAAACAGGTGGAGGTCGACTGTCAGCAA

TGTATGCTGGAGATCTTAGACACTGCAGGTACAGAAGAATTTACTGCCAT

GCGGGACCTGTACATGAAGAACGGGCAGGGCTTCGCTCTGGTATATTCCA

TCACCGCTCAGTCAACCTTTAACGACCTTCAGGATCTTCGCGAGCAGATC

CTACGCGTGAAAGATACAGAGGACGTCCCAATGATACTAGTGGGCAACAA

GTGTGACCTGGAGGATGAACGGGTTGTGGGCAAGGAGCAGGGTCAGAACC

TGGCCAGGCAGTGGTGCAACTGTGCCTTTCTGGAATCTAGCGCCAAGTCC

AAGATCAACGTAAACGAGATCTTCTACGACCTAGTACGTCAGATTAACCG

GAAGACACCTGTGGAGAAGAAGAAACCTAAGAAGAAATCCTGCCTGCTTC

TCTGA.

In some aspects, the constitutively active Rap1a is a variant of SEQ ID NO:2. In some aspects, the constitutively active Rap1a is 65, 70, 75, 80, 85, 90, 95, or 99 percent homologous to SEQ ID NO:2. In some aspects, variants of the constitutively active Rap1a must comprise the GAA shown underlined in SEQ ID NO:2 above. Thus, in some aspects, the percent identity of a variant of the constitutively active Rap1a can be 65, 70, 75, 80, 85, 90, 95, or 99 percent homologous to SEQ ID NO:2 and comprise the underlined GAA sequence shown above in SEQ ID NO:2. In some aspects, the codon present at the underlined GAA encodes a glutamic acid. In some aspects a variant of the constitutively active Rap1a can comprise any codon that encodes glutamic acid at the position of the underlined GAA in SEQ ID NO:2. The wild type Rap1a nucleic acid sequence encodes a glutamine at the corresponding sequence to the GAA location in SEQ ID NO:2. Thus, in some aspects, a nucleic acid sequence comprising a nucleic acid mutation that results in an amino acid change from glutamine to glutamic acid can be a constitutively active Rap1a nucleic acid sequence.

In some aspects, the constitutively active Rap1a is a variant of SEQ ID NO:3.

(SEQ ID NO: 3)

ATGCGTGAGTACAAGCTAGTGGTCCTTGGTTCAGGAGGCGTTGGGAAGTC

TGCTCTGACAGTTCAGTTTGTCAGGGAATTTTTGTTGAAAAATATGACCC

AACGATAGAAGATTCCTACAGAAAGCAAGTTGAAGTCGATTGCCAACAGT

GTATGCTCGAAATCCTGGATACTGCAGGGACAGAGCAATTTACAGCAATG

AGGGATTTGTATATGAAGAACGGCCAAGGTTTTGCACTAGTATATTCTAT

TACAGCTCAGTCCACGTTTAACGACTTACAGGACCTGAGGGAACAGATTT

TACGGGTTAAGGACACGGAAGATGTTCCAATGATTTTGGTTGGCAATAAA

TGTGACCTGGAAGATGAGCGAGTAGTTGGCAAAGAGCAGGGCCAGAATTT

AGCAAGACAGTGGTGTAACTGTGCCTTTTTAGAATCTTCTGCAAAGTCAA

AGATCAATGTTAATGAGATATTTTATGACCTGGTCAGACAGATAAATAGG

AAAACACCAGTGGAAAAGAAGAAGCCTAAAAAGAAATCATGTCTGCTGCT

CTAG

In some aspects, the constitutively active Rap1a is 65, 70, 75, 80, 85, 90, 95, or 99 percent homologous to SEQ ID NO:3. In some aspects, variants of the constitutively active Rap1a must comprise an CAA (underlined in SEQ ID NO:3) mutation to GAA. In some aspects, further mutations besides the CAA to GAA mutation can be present. Thus, in some aspects, the percent identity of a variant of the constitutively active Rap1a can be 65, 70, 75, 80, 85, 90, 95, or 99 percent homologous to SEQ ID NO:3 and at least comprise a mutation of the underlined CAA to a GAA sequence. Thus, the encoded active Rap1a comprises a glutamine to glutamic acid mutation.

In some aspects, the constitutively active Rap1a encodes active Rap1a. An example of active Rap1a can be

```
                                             (SEQ ID NO: 4)
MREYKLVVLGSGGVGKSALTVQFVQGIFVEKYDPTIEDSYRKQVEVDCQQ

CMLEILDTAGTEEFTAMRDLYMKNGQGFALVYSITAQSTFNDLQDLREQI

LRVKDTEDVPMILVGNKCDLEDERVVGKEQGQNLARQWCNCAFLESSAKS

KINVNEIFYDLVRQINRKTPVEKKKPKKKSCLLL.
```

In some aspects, the active Rap1a is 65, 70, 75, 80, 85, 90, 95, or 99 percent homologous to SEQ ID NO:4. In some aspects, variants of the active Rap1a must comprise the glutamic acid (E) in position 63, shown bolded in SEQ ID NO:4 above. Thus, in some aspects, the percent identity of a variant of the active Rap1a can be 65, 70, 75, 80, 85, 90, 95, or 99 percent homologous to SEQ ID NO:4 and at least comprise the bolded E amino acid shown above in SEQ ID NO:4. In some aspects, active Rap1a and wild type Rap1a are identical except for the Q→E mutation at position 63 in active Rap1A.

In some aspects, any of the disclosed nucleic acid constructs can further comprise a nucleic acid sequence encoding a marker. For example, disclosed are nucleic acid constructs comprising a nucleic acid sequence encoding a VMD2 promoter operably linked to a nucleic acid sequence encoding active Rap1a, further comprising a nucleic acid sequence encoding a marker.

In some aspects, the marker can be a label. In some aspects, marker genes can be the *E. coli* lacZ gene, which encodes β-galactosidase, or the gene encoding the green fluorescent protein (GFP). In some aspects, the marker can be a selectable marker. Examples of suitable selectable markers for mammalian cells are dihydrofolate reductase (DHFR), thymidine kinase, neomycin, neomycin analog G418, hydromycin, and puromycin.

In some aspects, the VMD2 promoter can be a constitutive promoter or inducible promoter. Inducible promoters are promoters whose activity can be controlled by specific environmental conditions or by the presence of a specific compound; they therefore make it possible to control the expression of the gene of interest (e.g. constitutively active Rap1a). In some aspects, the promoter can be derived from native genes or they may include synthetic DNA segments.

In an aspect, disclosed herein are composition comprising an inducible promoter within the constructs disclosed herein, so that transcription of selected genes (e.g. constitutively active Rap1a) can be turned on and off. This can minimize cellular toxicity that can sometimes be caused by expression of cytotoxic viral proteins, increasing the stability of the cells containing the vectors. For example, high levels of expression of VSV-G (envelope protein) and Vpr can be cytotoxic (Yee, J.-K., et al., Proc. Natl. Acad. Sci., 91:9654-9568 (1994) and, therefore, expression of these proteins in packaging cells of the invention can be controlled by an inducible operator system, such as the inducible Tet operator system (GIBCO BRL, Carlsbad, California), allowing for tight regulation of gene expression (i.e., generation of retroviral particles) by the concentration of tetracycline in the culture medium. That is, with the Tet operator system, in the presence of tetracycline, the tetracycline is bound to the Tet transactivator fusion protein (tTA), preventing binding of tTA to the Tet operator sequences and allowing expression of the gene under control of the Tet operator sequences (Gossen et al. (1992) PNAS 89:5547-5551), which is incorporated by reference herein in their entirety for its teachings of the tTA and allowing expression of the gene under control of the Tet operator sequences. In the absence of tetracycline, the tTA binds to the Tet operator sequences preventing expression of the gene under control of the Tet operator.

Examples of other inducible operator systems that can be used for controlled expression of the protein, can include 1) inducible eukaryotic promoters responsive to metal ions (e.g., the metallothionein promoter), glucocorticoid hormones and 2) the LacSwitch™ Inducible Mammalian Expression System (Stratagene) (La Jolla, California) of *E. coli*. Briefly, in the *E. coli* lactose operon, the Lac repressor binds as a homotetramer to the lac operator, blocking transcription of the lac2 gene. Inducers such as allolactose (a physiologic inducer) or isopropyl-β-D-thiogalactoside (IPTG, a synthetic inducer) bind to the Lac repressor, causing a conformational change and effectively decreasing the affinity of the repressor for the operator. When the repressor is removed from the operator, transcription from the lactose operon resumes.

C. Vectors

Disclosed are vectors comprising any of the nucleic acid constructs disclosed herein.

The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

In some aspects, the vector can be a viral vector. For example, the viral vector can be an adeno-associated viral vector. In some aspects, the vector can be a non-viral vector, such as a DNA based vector.

i. Viral and Non-Viral Vectors

There are a number of compositions and methods which can be used to deliver the disclosed nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be any nucleotide construction used to deliver genes or gene fragments into cells (e.g., a plasmid), or as part of a general strategy to deliver genes or gene fragments, e.g., as part of recombinant retrovirus or adenovirus (Ram et al. Cancer Res. 53:83-88, (1993)). For example, disclosed herein are expression vectors comprising a nucleic acid sequence capable of encoding encoding a VMD2 promoter operably linked to a nucleic acid sequence encoding Rap1a.

The "control elements" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif) or pSPORT1 plasmid (Gibco BRL, Gaithersburg, Md.) and the like may be used. If it is necessary to generate a cell line that contains multiple copies of the sequence encoding a polypeptide, vectors based on SV40 or EBV may be advantageously used with an appropriate selectable marker.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Optionally, the promoter or enhancer region can act as a constitutive promoter or enhancer to maximize expression of the polynucleotides of the invention. In certain constructs the promoter or enhancer region be active in all eukaryotic cell types, even if it is only expressed in a particular type of cell at a particular time.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The expression vectors can include a nucleic acid sequence encoding a marker product. This marker product can be used to determine if the gene has been delivered to the cell and once delivered is being expressed. Marker genes can include, but are not limited to the *E. coli* lacZ gene, which encodes β-galactosidase, and the gene encoding the green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

Another type of selection that can be used with the composition and methods disclosed herein is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

As used herein, plasmid or viral vectors are agents that transport the disclosed nucleic acids, such as a nucleic acid sequence capable of encoding one or more of the disclosed peptides into the cell without degradation and include a promoter yielding expression of the gene in the cells into which it is delivered. In some embodiments the nucleic acid sequences disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities (i.e., ability to introduce genes) than chemical or physical methods of introducing genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)) the teachings of which are incorporated herein by reference in their entirety for their teaching of methods for using retroviral vectors for gene therapy. Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol., 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. Optionally, both the E1 and E3 genes are removed from the adenovirus genome.

Another type of viral vector that can be used to introduce the polynucleotides of the invention into a cell is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, CA, which can contain the herpes simplex virus thymidine kinase gene, HSV-tk, or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

The inserted genes in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Felgner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

D. Compositions

Disclosed are compositions comprising the disclosed nucleic acid constructs or vectors. Disclosed are compositions comprising a nucleic acid construct, wherein the nucleic acid construct comprises a nucleic acid sequence encoding a VMD2 promoter operably linked to constitutively active Rap1a nucleic acid sequence. Disclosed are compositions comprising a nucleic acid construct, wherein the nucleic acid construct comprises a nucleic acid sequence encoding a VMD2 promoter operably linked to a nucleic acid sequence encoding active Rap1a. Also disclosed are compositions comprising a vector, such as a viral vector, comprising a nucleic acid construct, wherein the nucleic acid construct comprises a nucleic acid sequence encoding a VMD2 promoter operably linked to a nucleic acid sequence encoding active Rap1a.

The disclosed compositions can further comprise a pharmaceutically acceptable carrier.

1. Delivery of Compositions

In the methods described herein, delivery (or administration) of the compositions to cells can be via a variety of mechanisms. As defined above, disclosed herein are compositions comprising any one or more of the peptides, nucleic acids, and/or vectors described herein can be used to produce a composition which can also include a carrier such as a pharmaceutically acceptable carrier. For example, disclosed are pharmaceutical compositions, comprising the peptides disclosed herein, and a pharmaceutically acceptable carrier.

For example, the compositions described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

The disclosed delivery techniques can be used not only for the disclosed compositions but also the disclosed nucleic acid constructs and vectors.

E. Recombinant Cells

Disclosed are recombinant cells comprising one or more of the disclosed nucleic acid constructs or vectors. For example, disclosed are recombinant cells comprising a nucleic acid construct, wherein the nucleic acid construct comprises a nucleic acid sequence encoding a VMD2 promoter operably linked to a nucleic acid sequence encoding Rap1a.

In some aspects, the cell is a mammalian cell. In some aspects, the cell is a retinal pigment epithelial (RPE) cell.

F. Methods of Treating

Disclosed are methods of treating a subject having age-related macular degeneration comprising administering one or more of the disclosed nucleic acid constructs, vectors, or compositions to a subject in need thereof.

In some aspects, the compositions are administered via subretinal administration. In some aspects, the compositions are administered via intravitreal administration. In some aspects, the compositions are administered via intravitreal administration and the composition comprises the 7M8 AAV vector construct at a concentration of $5\times10^{12}$ viral particles. Other known routes of administration can also be used with the disclosed methods.

In some aspects of the disclosed methods of treating, expression of active Rap1 can be increased in the subject without increasing markers of autophagy or apoptosis. For example, disclosed are methods of treating a subject having age-related macular degeneration comprising administering one or more of the disclosed nucleic acid constructs, vectors, or compositions to a subject in need thereof, wherein expression of Rap1 is increased in the subject without increasing markers of autophagy or apoptosis in the subject. In some aspects, expression of active Rap1 can be increased in retinal epithelial cells of the subject without increasing markers of autophagy or apoptosis. For example, disclosed are methods of treating a subject having age-related macular degeneration comprising administering one or more of the disclosed nucleic acid constructs, vectors, or compositions to a subject in need thereof, wherein expression of active Rap1 can be increased in retinal epithelial cells of the subject without increasing markers of autophagy or apoptosis in retinal epithelial cells of the subject.

In some aspects, the active Rap1a can be expressed at levels at least two times the levels of active Rap1a expressed in control subjects. In some aspects, the active Rap1a can be expressed at levels at least 2.5, 3, 3.5, 4, 4.5, 5, 5.5, 6, 6.5, 7, 7.5, 8, 8.5, 9, 9.5, or 10 times the levels of active Rap1a expressed in control subjects. In some aspects, the active Rap1a can be expressed at levels at least 10, 20, 30, 40, or 50 times the levels of active Rap1a expressed in control subjects.

In some aspects, the optimal dose of one of the disclosed vectors can be $5\times10^8$ viral particles for subretinal injections. In some aspects, the dose can be, but is not limited to, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $2\times10^9$, $3\times10^9$, $4\times10^9$, $5\times10^9$, $6\times10^9$, $7\times10^9$, $8\times10^9$, or $9\times10^9$. In some aspects, particularly with intravitreal injections, doses can be higher. For example, higher doses can be, but are not limited to, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$.

Disclosed are methods of treating a subject having age-related macular degeneration comprising administering one or more of the disclosed nucleic acid constructs, vectors, or compositions to a subject in need thereof in combination with administering one or more anti-VEGF agents to the subject. Disclosed are methods of treating a subject having age-related macular degeneration comprising administering one or more of the disclosed nucleic acid constructs, vectors, or compositions to a subject in need thereof, and further comprising administering one or more anti-VEGF agents to the subject. In some aspects, the nucleic acid construct, vector, or composition and the anti-VEGF agent can be administered simultaneously. In some aspects, the nucleic acid construct, vector, or composition and the anti-VEGF agent can be co-administered in a single formulation. In some aspects, the nucleic acid construct, vector, or composition and the anti-VEGF agent can be administered in separate formulations. Thus, regardless of whether the nucleic acid construct, vector, or composition and the anti-VEGF agent are formulated together in a single formulation or in separate formulations, they can still be administered simultaneously. Simultaneous administration can include administering the nucleic acid construct, vector, or composition and the anti-VEGF agent at the exact same time, within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes of each other.

G. Methods of Inhibiting

Disclosed are methods of inhibiting choroidal neovascularization (CNV) comprising administering to a subject any of the disclosed nucleic acid constructs, vectors, or compositions.

Also disclosed are methods of reducing CNV comprising administering to a subject any of the disclosed nucleic acid constructs, vectors, or compositions. Disclosed are methods of are methods of reducing CNV is a subject comprising administering one or more of the disclosed nucleic acid constructs, vectors, or compositions to a subject in need thereof.

In some aspects, the administration in the disclosed methods is a subretinal or intravitreal administration. In some aspects, the administration can be by intravenous route.

In some aspects of the disclosed methods of treating, expression of active Rap1a can be increased in the subject without increasing markers of autophagy or apoptosis. For example, disclosed are methods of are methods of reducing CNV is a subject comprising administering one or more of the disclosed nucleic acid constructs, vectors, or compositions to a subject in need thereof, wherein expression of active Rap1 is increased in the subject without increasing markers of autophagy or apoptosis in the subject. In some aspects, expression of active Rap1 can be increased in retinal epithelial cells of the subject without increasing markers of autophagy or apoptosis. For example, disclosed are methods of are methods of reducing CNV is a subject comprising administering one or more of the disclosed nucleic acid constructs, vectors, or compositions to a subject in need thereof, wherein expression of active Rap1 is increased in retinal epithelial cells of the subject without increasing markers of autophagy or apoptosis in the retinal epithelial cells of the subject.

In some aspects, the active Rap1a can be expressed at levels at least two times the levels of active Rap1a expressed in control subjects. In some aspects, the active Rap1a can be expressed at levels at least 2.5, 3, 3.5, 4, 4.5, 5, 5.5, 6, 6.5, 7, 7.5, 8, 8.5, 9, 9.5, or 10 times the levels of active Rap1a expressed in control subjects. In some aspects, the active Rap1a can be expressed at levels at least 10, 20, 30, 40, or 50 times the levels of active Rap1a expressed in control subjects.

In some aspects, the optimal dose of one of the disclosed vectors can be $5\times10^8$ viral particles for subretinal injections. In some aspects, the dose can be, but is not limited to, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $2\times10^9$, $3\times10^9$, $4\times10^9$, $5\times10^9$, $6\times10^9$, $7\times10^9$, $8\times10^9$, or $9\times10^9$. In some aspects, particularly with intravitreal injections, doses can be higher. For example, higher doses can be, but are not limited to, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$.

Disclosed are methods of inhibiting or reducing CNV comprising administering to a subject any of the disclosed nucleic acid constructs, vectors, or compositions, and further comprising administering one or more anti-VEGF agents to the subject. In some aspects, the nucleic acid construct, vector, or composition and the anti-VEGF agent can be administered simultaneously. In some aspects, the nucleic acid construct, vector, or composition and the anti-VEGF agent can be co-administered in a single formulation. In some aspects, the nucleic acid construct, vector, or composition and the anti-VEGF agent can be administered in separate formulations. Thus, regardless of whether the nucleic acid construct, vector, or composition and the anti-VEGF agent are formulated together in a single formulation or in separate formulations, they can still be administered simultaneously. Simultaneous administration can include administering the nucleic acid construct, vector, or composition and the anti-VEGF agent at the exact same time, within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes of each other.

H. Methods of Reducing Inflammatory Signaling

Disclosed are methods of reducing inflammatory signaling in choroid tissue comprising administering to a subject any of the disclosed nucleic acid constructs, vectors, or compositions.

In some aspects, the administration in the disclosed methods is a subretinal, intravitreal, or intravenous administration.

In some aspects of the disclosed methods, expression of active Rap1a can be increased in the subject without increasing markers of autophagy or apoptosis. For example, disclosed are methods of reducing inflammatory signaling in choroid tissue comprising administering to a subject any of the disclosed nucleic acid constructs, vectors, or compositions, wherein expression of active Rap1a is increased in the subject without increasing markers of autophagy or apoptosis in the subject. In some aspects, expression of active Rap1a can be increased in retinal epithelial cells of the subject without increasing markers of autophagy or apoptosis. For example, disclosed are methods of reducing inflammatory signaling in choroid tissue comprising administering to a subject any of the disclosed nucleic acid constructs, vectors, or compositions, wherein expression of active Rap1a can be increased in retinal epithelial cells of the subject without increasing markers of autophagy or apoptosis in retinal epithelial cells of the subject.

In some aspects, the active Rap1a can be expressed at levels at least two times the levels of active Rap1a expressed in control subjects. In some aspects, the active Rap1a can be expressed at levels at least 2.5, 3, 3.5, 4, 4.5, 5, 5.5, 6, 6.5, 7, 7.5, 8, 8.5, 9, 9.5, or 10 times the levels of active Rap1a expressed in control subjects. In some aspects, the active Rap1a can be expressed at levels at least 10, 20, 30, 40, or 50 times the levels of active Rap1a expressed in control subjects.

In some aspects, the optimal dose of one of the disclosed vectors can be $5\times10^8$ viral particles for subretinal injections. In some aspects, the dose can be, but is not limited to, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $2\times10^9$, $3\times10^9$, $4\times10^9$, $5\times10^9$, $6\times10^9$, $7\times10^9$, $8\times10^9$, or $9\times10^9$. In some aspects, particularly with intravitreal injections, doses can be higher. For example, higher doses can be, but are not limited to, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$.

Disclosed are methods of reducing inflammatory signaling in choroid tissue comprising administering to a subject any of the disclosed nucleic acid constructs, vectors, or compositions, and further comprising administering one or more anti-VEGF agents to the subject. In some aspects, the nucleic acid construct, vector, or composition and the anti-VEGF agent can be administered simultaneously. In some aspects, the nucleic acid construct, vector, or composition and the anti-VEGF agent can be co-administered in a single formulation. In some aspects, the nucleic acid construct, vector, or composition and the anti-VEGF agent can be administered in separate formulations. Thus, regardless of whether the nucleic acid construct, vector, or composition and the anti-VEGF agent are formulated together in a single formulation or in separate formulations, they can still be administered simultaneously. Simultaneous administration can include administering the nucleic acid construct, vector, or composition and the anti-VEGF agent at the exact same time, within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes of each other.

I. Methods of Reducing VEGF Expression

Disclosed are methods of reducing VEGF expression in choroidal tissue comprising administering to a subject any of the disclosed nucleic acid constructs, vectors, or compositions.

In some aspects, the administration in the disclosed methods is a subretinal, intravitreal, or intravenous administration.

In some aspects of the disclosed methods of treating, expression of active Rap1a can be increased in the subject without increasing markers of autophagy or apoptosis. For example, disclosed are methods of reducing VEGF expression in choroidal tissue comprising administering to a subject any of the disclosed nucleic acid constructs, vectors, or compositions, wherein expression of active Rap1a is increased in the subject without increasing markers of autophagy or apoptosis in the subject. In some aspects, expression of active Rap1a can be increased in retinal epithelial cells of the subject without increasing markers of autophagy or apoptosis. For example, disclosed are methods of reducing VEGF expression in choroid tissue comprising administering to a subject any of the disclosed nucleic acid constructs, vectors, or compositions wherein expression of active Rap1a can be increased in retinal epithelial cells of the subject without increasing markers of autophagy or apoptosis in retinal epithelial cells of the subject.

In some aspects, the active Rap1a can be expressed at levels at least two times the levels of active Rap1a expressed in control subjects. In some aspects, the active Rap1a can be expressed at levels at least 2.5, 3, 3.5, 4, 4.5, 5, 5.5, 6, 6.5, 7, 7.5, 8, 8.5, 9, 9.5, or 10 times the levels of active Rap1a expressed in control subjects. In some aspects, the active Rap1a can be expressed at levels at least 10, 20, 30, 40, or 50 times the levels of active Rap1a expressed in control subjects.

In some aspects, the optimal dose of one of the disclosed vectors can be $5\times10^8$ viral particles for subretinal injections. In some aspects, the dose can be, but is not limited to, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $2\times10^9$, $3\times10^9$, $4\times10^9$, $5\times10^9$, $6\times10^9$, $7\times10^9$, $8\times10^9$, or $9\times10^9$. In some aspects, particularly with intravitreal injections, doses can be higher. For example, higher doses can be, but are not limited to, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$.

Disclosed are methods of reducing VEGF expression in choroidal tissue comprising administering to a subject any of the disclosed nucleic acid constructs, vectors, or compositions, and further comprising administering one or more anti-VEGF agents to the subject. In some aspects, the nucleic acid construct, vector, or composition and the anti-VEGF agent can be administered simultaneously. In some aspects, the nucleic acid construct, vector, or composition and the anti-VEGF agent can be co-administered in a single formulation. In some aspects, the nucleic acid construct, vector, or composition and the anti-VEGF agent can be administered in separate formulations. Thus, regardless of whether the nucleic acid construct, vector, or composition and the anti-VEGF agent are formulated together in a single formulation or in separate formulations, they can still be administered simultaneously. Simultaneous administration can include administering the nucleic acid construct, vector, or composition and the anti-VEGF agent at the exact same time, within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes of each other.

J. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising one or more of the disclosed nucleic acid constructs, vectors, or compositions. Also disclosed are kits for making any of the disclosed vectors, the kit comprising a nucleic acid construct comprising a nucleic acid sequence encoding a VMD2 promoter operably linked to a nucleic acid sequence encoding Rap1a. The kits also can contain a vector backbone.

Examples

Activation of Rap1a, a GTPase protein, was found to protect the barrier function of the RPE from inflammatory stress. In a murine model of laser-induced choroidal neovascularization (CNV), Rap1 activity was decreased in the RPE and choroid tissues, but delivery of intravitreal 8-CPT-2Me-cAMP to activate endogenous Rap1 inhibited CNV induced by laser. Gene therapy was investigated as an approach to target the RPE specifically and potentially reduce the number of treatments required by intravitreal delivery. Because of lack of pathogenicity, the low immunogenicity, relatively long-term transgene expression compared to intravitreal neutralizing antibodies or pharmacologic agents, and high transduction efficiency, vectors of adenovirus-associated virus (AAV) are becoming promising tools to treat retinal degeneration. To increase active Rap1a in the RPE, a constitutively active Rap1a (CARap1a) was delivered in a self-complementary AAV2 (sc-AAV2) viral vector driven by the RPE65 promoter (sc-AAV2-RPE65) and was found to reduce experimental CNV in Rap1b deficient mice but not in wild type mice.

The insufficient reduction of CNV in wild type mice by the sc-AAV2-RPE65 delivered CARap1a was predicted to be related to the weak transcriptional activity of the RPE65 promoter. To test this possibility, the RPE65 promoter was compared to another specific promoter of the RPE, vitelliform macular dystrophy-2 (VMD2). The two promoters, RPE65 and VMD2, were compared in driving the expression of CARap1a in the RPE and in reducing experimental CNV in wild type mice. In this study, the effect of the expression of exogenous CARap1a was also evaluated and compared in eyes treated with the two different promoters, RPE65 and VMD2.

1. Results

Generation of self-complementary adeno-associated virus 2 (sc-AAV2) driven by VMD2 promoter. A self-complementary adeno-associated virus 2 (sc-AAV2) with a green fluorescent protein (GFP) tag was used in this study. The sc-AAV2 driven by a murine RPE65 promoter expressing either GFP alone or active Rap1a (CARap1a) (FIG. 1A) was generated. To compare the transcriptional activity of RPE65 and VMD2 promoters in delivering active Rap1a in RPE, a murine VMD2 promoter was cloned into sc-AAV2 vector to replace the RPE65 promoter, driving either GFP or GFP and active Rap1a (CARap1a) (FIG. 1B).

Figures 2A, 2B:
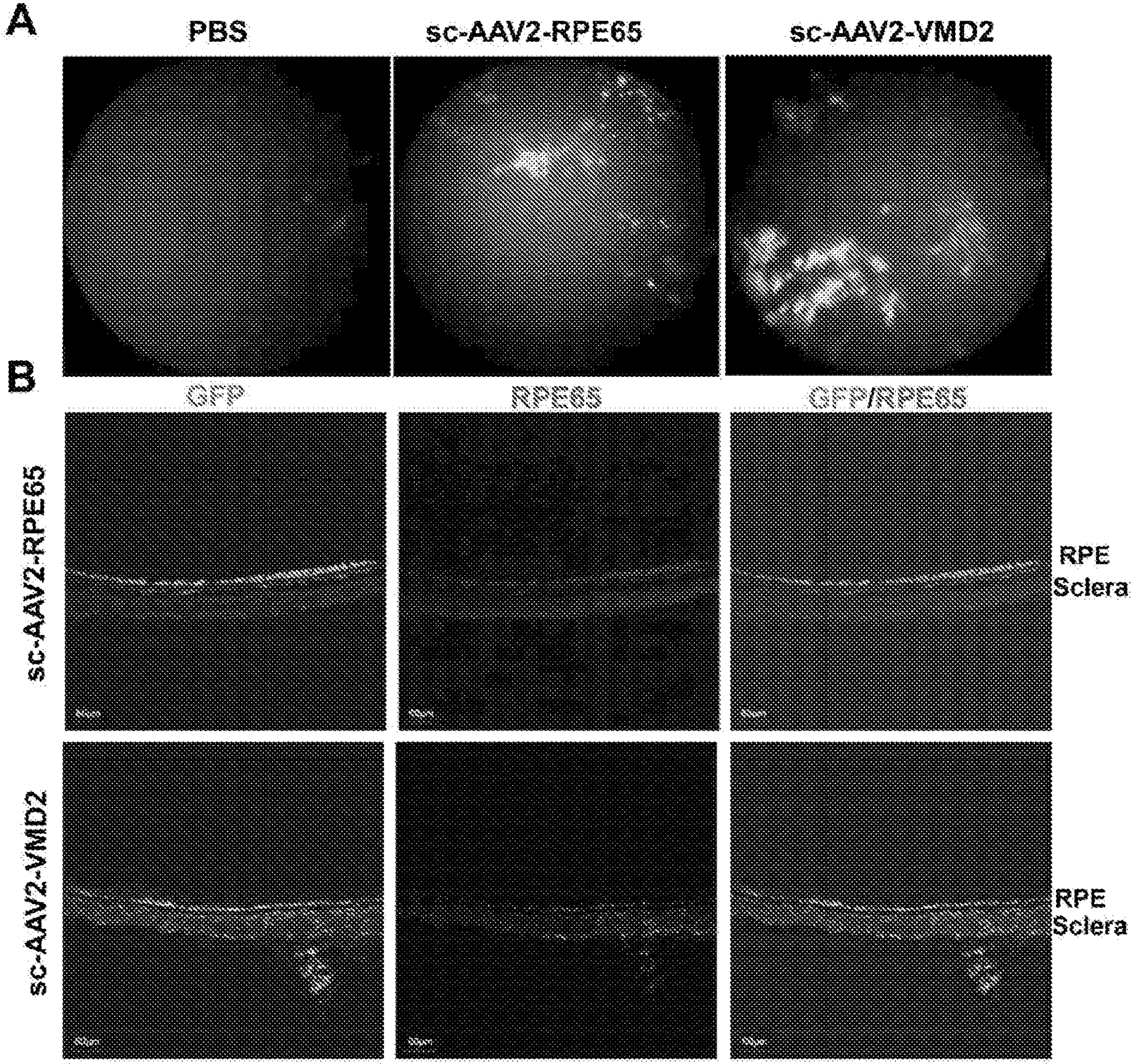
FIGS. 2A and 2B show an in vivo analysis of sc-AAV2 transduction in RPE of wild type mice. (A) Micron IV retinal imaging of GFP and (B) immunostaining of GFP and RPE65 in retinal cryosections of wild type mice 5 weeks after injection of sc-AAV2-RPE65-GFP or sc-AAV2-VMD2-GFP vectors at dose of $5\times10^8$ viral particle/μl.

In vivo analysis of sc-AAV2 transduction and Rap1 expression. To determine the viral transduction efficiency, sc-AAV2-RPE65 or sc-AAV2-VMD2 virus at $5\times10^8$ viral particle/μl was delivered into the subretinal space of both eyes of 6-week-old wild type mice. Viral transduction was determined by GFP visualization using a Micron IV retinal live imaging system at week 5 after injection. As shown in FIG. 2A, both sc-AAV2-RPE65 and sc-AAV2-VMD2 showed GFP expression, whereas PBS-injected eyes did not show GFP expression. To confirm the viral transduction targeted the RPE, GFP positive eyes were harvested and the RPE/choroid cryosections were immunolabeled with GFP and RPE65 antibodies. Both sc-AAV2-RPE65 and sc-AAV2-VMD2 virus treated eyes showed GFP colabeling with RPE65 (FIG. 2B), indicating both viral vectors can transduce the RPE of wild type mice. To further determine the specificity of AAV2 viral transduction, GFP immunostaining was performed in whole retinal cryosections. In sc-AAV2-RPE65 treated retina, GFP immunolabeling was not only located in the layer of the RPE, but also in the retinal ganglion cells and photoreceptor outer segments (PR/OS); however, in sc-AAV2-VMD2 treated retina, GFP immunolabeling was only found in the layer of the RPE and the PR/OS (FIG. 3A), showing the sc-AAV2-VMD2 vector had greater specificity in transducing the RPE.

Figures 3A, 3B, 3C:
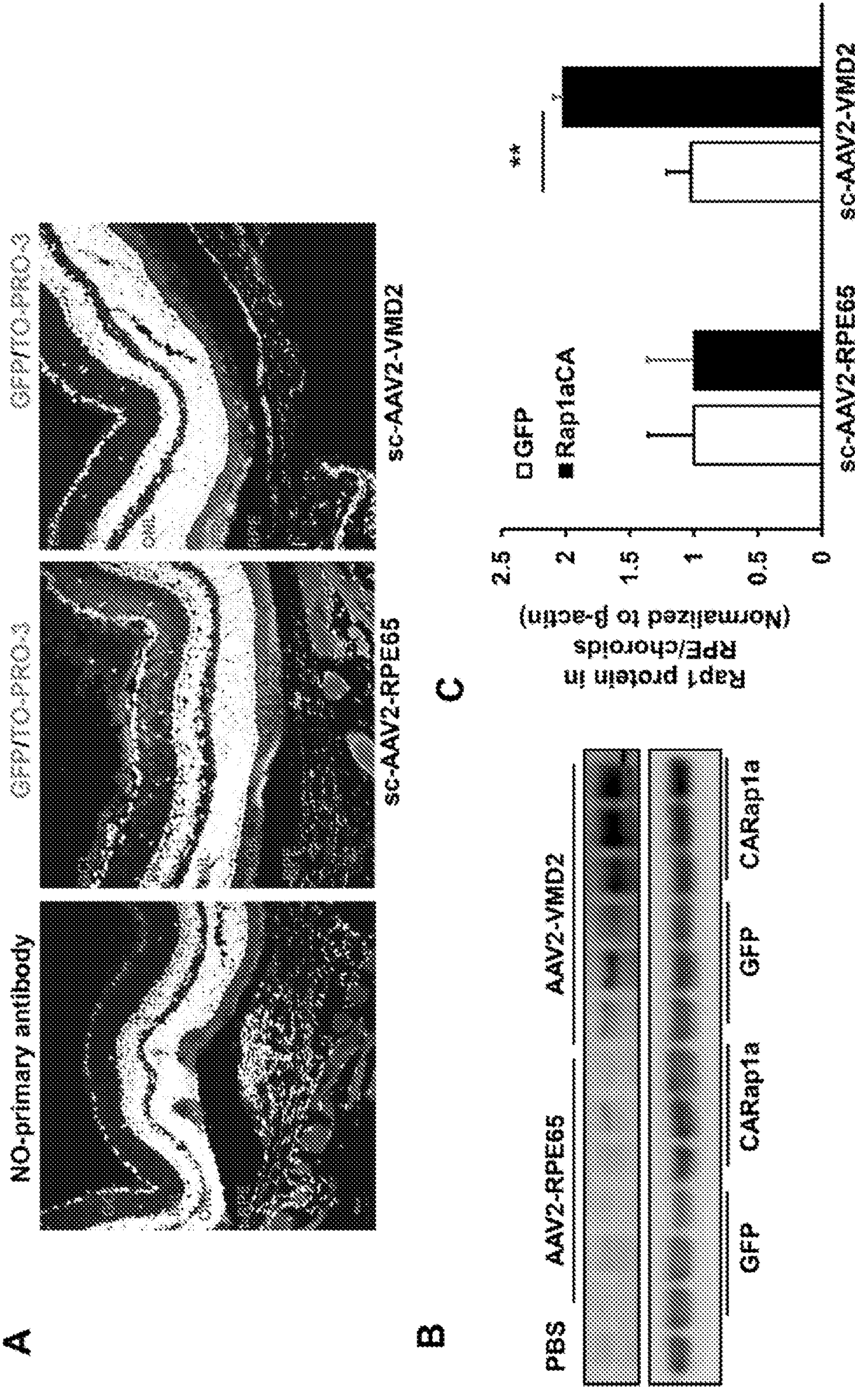
FIGS. 3A, 3B, and 3C show sc-AAV2-VMD2 vector shows more specific GFP transduction and greater Rap1 expression in the RPE. (A) IHC of GFP in retinal cryosections (B-C) Western blots of Rap1 and β-actin in RPE/choroids (B, representative gel image and C, quantification of densitometry) of wild type mice injected with either sc-AAV2-RPE65 or sc-AAV2-VMD2 (**$p<0.01$ vs. sc-AAV2-VMD2-GFP, n=5-6).

By western blots using an antibody to total Rapt, Rap1a protein levels were determined in RPE/choroid tissues from GFP-positive eyes 5 weeks after subretinal injections. As shown in FIGS. 3B and C, Rapt protein was significantly increased in sc-AAV2-CARap1a treated RPE/choroid lysates compared to sc-AAV2-VMD2-GFP. However, eyes treated with sc-AAV2-RPE65-CARap1a did not show increased Rapt protein compared to sc-AAV2-RPE65-GFP. The data in FIGS. 2 and 3 provide evidence that both sc-AAV2-RPE65 and sc-AAV2-VMD2 transduced the RPE of wild type mice, but only sc-AAV2-VMD2 efficiently drove Rap1a expression.

Figures 4A, 4B:
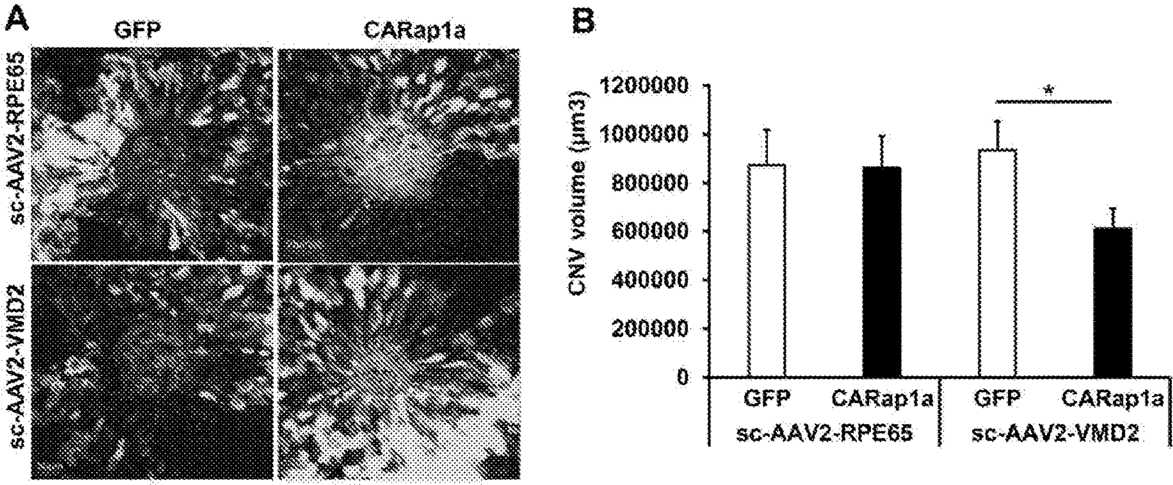
FIGS. 4A and 4B show expression of active Rap1a in RPE by sc-AAV2-VMD2-CARap1a reduces choroidal neovascularization (CNV) in wild type mice in a laser induced CNV model. (A) Representative images of RPE/choroid flat mounts and (B) quantification of CNV lesion (*$p<0.05$ vs. sc-AAV2-VMD2, n=40 spots from 12 mice).

Expression of active Rap1a in RPE delivered by sc-AAV2-VMD2 reduces CNV in wild type mice. Expression of active Rap1a in RPE by sc-AAV2-RPE65 reduced laser-induced CNV in Rapt deficient mice but not in wild type mice. It was determined if increased Rap1a in RPE by sc-AAV2-VMD2 would reduce CNV induced by laser in wild type mice comparing outcomes to mice with subretinal injections of sc-AAV2-RPE65. To compare each experimental vector and its respective control, we used ANOVA analysis, which considered each CNV lesion as an individual data point. Consistent with previous findings, sc-AAV2-RPE65-CARap1a did not reduce CNV compared to sc-AAV2-RPE65-GFP; however, compared to sc-AAV2-VMD2-GFP, sc-AAV2-VMD2-CARap1a significantly reduced CNV by ANOVA analysis (p=0.026) (FIG. 4). To further confirm if each CNV lesion could be considered as an individual data point, the statistical analysis was run using a mixed effects linear regression to compare sc-AAV2-VMD2-CARap1a and sc-AAV2-VMD2-GFP. The amount of correlation among the spots within the same eye was measured with the intraclass correction coefficient (ICC), which was ICC=0.16, 95% CI (0.02, 0.53), indicating that an ordinary two sample ANOVA would not be appropriate, as it requires that all observations, or spots, be independent. By a mixed effects linear regression analysis, the mean±SE in the sc-AAV2-VMD2-CARap1a group was 619,928±124,932, and in the control sc-AAV2-VMD2-GFP was 952,091±124.932; compared to sc-AAV2-VMD2-GFP, there was a statistically significant difference (mean difference, 336,162, 95% CI: 2,454 to 647,778; p=0.05). The mixed effects linear repression analysis supported that sc-AAV2-VMD2-CARap1a significantly reduced CNV in wild type mice.

Figures 5A, 5B, 5C, 5D:
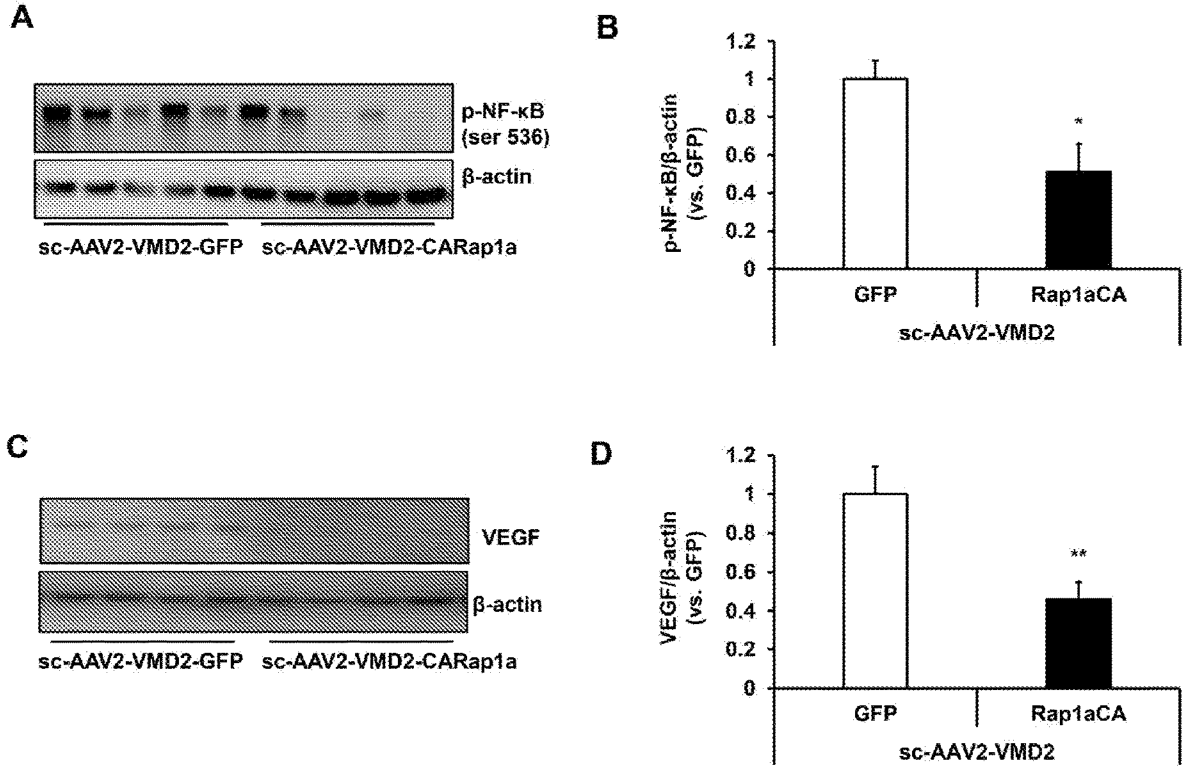
FIGS. 5A-5D show expression of active Rap1a in RPE by sc-AAV2-VMD2-CARap1a reduces inflammation and VEGF in RPE/choroids. Western blots of (A-B) phosphorylated NF-κB and (C-D) VEGF in RPE/choroids of sc-AAV2-VMD2 injected wild type mice 7 days after laser treatment (A and C, representative gel images and B and D, quantification of densitometry; *p<0.05, **p<0.01 vs. sc-AAV2-VMD2-GFP; n=5-6).

Expression of active Rap1a in RPE reduces inflammatory signaling and VEGF expression in RPE/choroid tissues. Both inflammation and VEGF signaling are involved in the pathogenesis of AMD. It was previously found that laser treatment significantly increased TNFα in RPE/choroid tissues, and inhibition of TNFα by an intravitreal neutralizing antibody reduced CNV. It was determined if increased active Rap1a in the RPE by sc-AAV2-VMD2-CARap1a would reduce inflammation by employing TNFα mediated signaling as a test example. Phosphorylation of nuclear factor kappa of activated B cells (NF-κB), a downstream effector of TNFα, was measured in RPE/choroid lysates by western blots. As shown in FIGS. 5A and B, phosphorylated NF-κB (p-NF-κB) was significantly decreased by sc-AAV2-VMD2-CARap1a compared to sc-AAV2-VMD2-GFP. In the same tissue lysates, VEGF protein was also significantly decreased by sc-AAV2-VMD2-CARap1a compared to sc-AAV2-VMD2-CARap1a (FIGS. 5C and D).

Figures 6A, 6B, 6C, 6D:
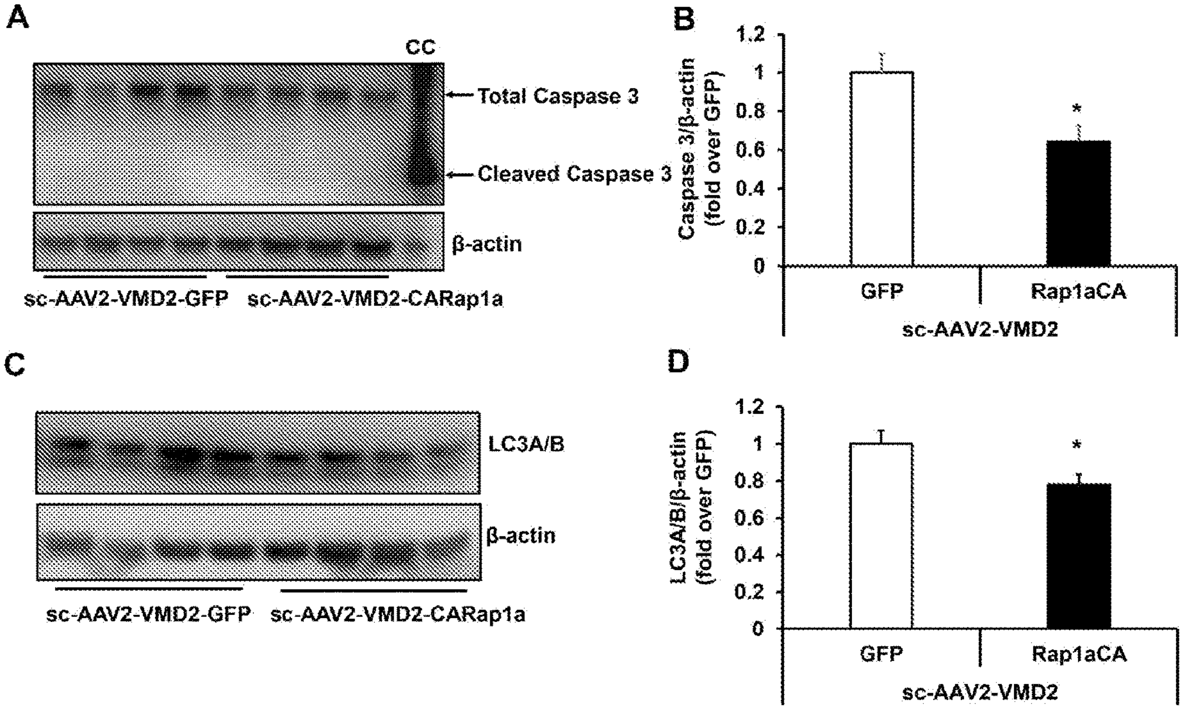
FIGS. 6A-6D show expression of active Rap1a in RPE by sc-AAV2-VMD2-CARap1a does not activate apoptosis and autophagy. Western blots of (A-B) caspase 3 and (C-D) LC3A/B in RPE/choroids of sc-AAV2-VMD2 injected wild type mice 7 days after laser treatment (A and C, representative gel images and B and D, quantification of densitometry; *p<0.05 vs. sc-AAV2-VMD2-GFP; n=5-6; CC, cytochrome C treated cell lysate).

Expression of active Rap1a in RPE reduces caspase 3 and LC3A/B in RPE/choroid tissues. The results in FIGS. 3 and 4 provide evidence to support the hypothesis that the sc-AAV2-VMD2 vector efficiently drove active Rap1a expression specifically in the RPE and reduced CNV in wild type mice. It was then determined if increased active Rap1a in RPE by sc-AAV2-VMD2-CARap1a would overwhelm RPE homeostasis, since delivering a protein may overwhelm the cell's ability to maintain its viability. Caspase 3 and cleaved caspase 3, an apoptotic maker, and LC3A/B, an autophagic regulator, were measured in RPE/choroid lysates from sc-AAV2-VMD2 treated eyes. As shown in FIG. 6, compared to sc-AAV2-VMD2-GFP, total caspase 3 (FIGS. 6A and B) and LC3A/B (FIGS. 6C and D) in RPE/choroid tissues were significantly decreased by sc-AAV2-VMD2-CARap1a. Cleaved caspase 3 was not detected in RPE/choroid tissues from either group. Taken together, the data shown in FIG. 6 indicate that expression of active Rap1a in RPE by sc-AAV2-VMD2 does not cause activation of caspase 3 and excessive activation of autophagy.

Figures 7A, 7B, 7C, 7D, 7E, 7F, 7G, 7H, 7I, 7J, 7K:
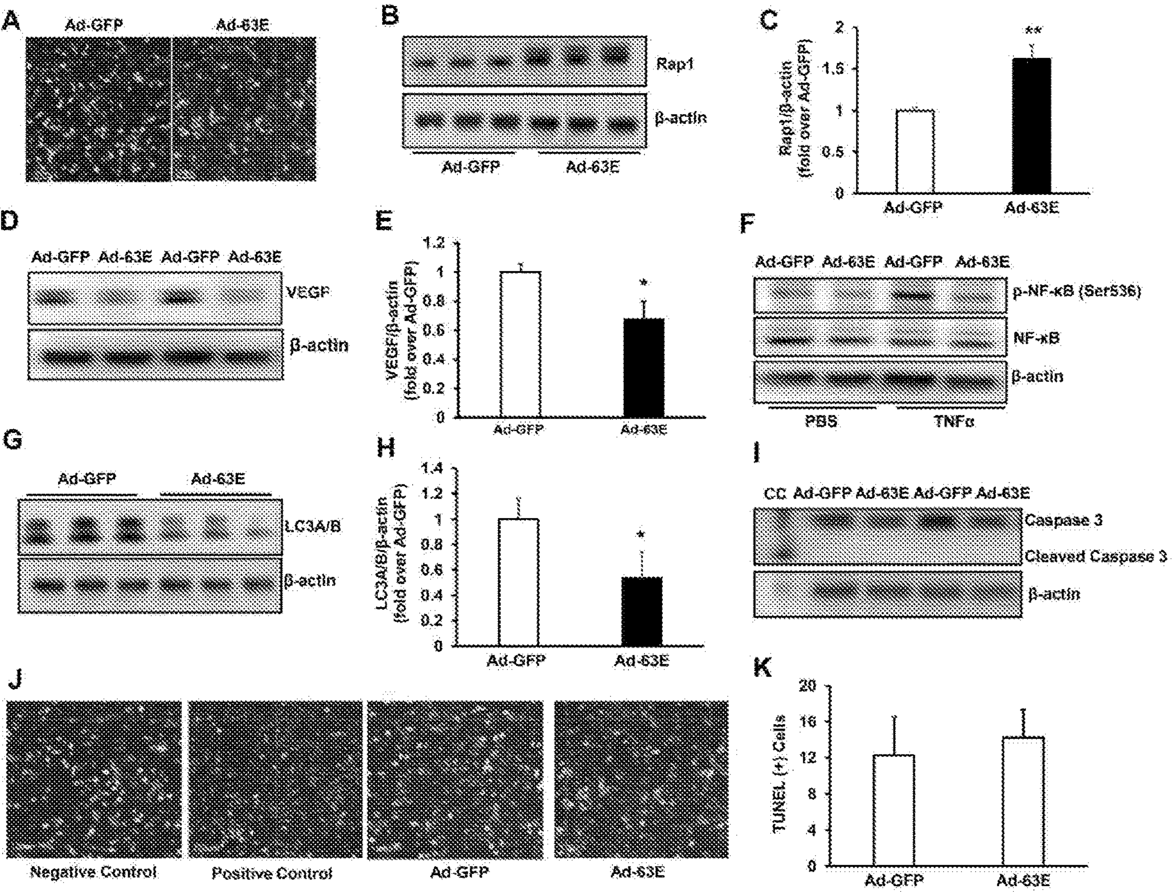
FIGS. 7A-7K show expression of active Rap1a in RPE by adenovirus transduction reduces VEGF and NF-κB activation without increasing autophagy and cell death. (A) Virus transduced RPE and western blots of (B-C) Rap1 protein, (D-E) VEGF protein, (F) phosphorylated NF-κB (p-NF-κB) and total NF-κB, (G-H) LC3A/B protein and (I) caspase 3 and cleaved caspase 3; and (J-K) TUNEL staining in human RPE transduced with adenovirus expressing GFP (Ad-GFP) or GFP and constitutively active Rap1a (Ad-63E) (*p<0.05, **p<0.01 vs. Ad-GFP; n=3; CC in I refers to cytochrome C treated cell lysate).

Expression of active Rap1a in RPE reduces VEGF, TNFα-induced NF-κB activation and LC3A/B without causing cell death. To further assess the effects of active Rap1a on VEGF expression, activation of inflammatory signaling, autophagy and cell death, a series of experiments were performed in cultured human RPE transduced with adenovirus expressing the Rap1a Q63E mutant that constitutively activates Rap1a (Ad-63E) or control adenovirus expressing only GFP (Ad-GFP). The viral transduction was monitored by GFP visualization. Forty-eight hours after viral transduction, about 80% of the RPE were GFP positive (FIG. 7A), and total Rap1 protein measured by western blots was increased in RPE transduced with Ad-63E compared to Ad-GFP (FIGS. 7B and C). In Ad-63E transduced RPE, VEGF protein (FIGS. 7D and E), TNFα-induced p-NF-κB (FIG. 7F) and LC3A/B (FIGS. 7G and H) were significantly reduced compared to Ad-GFP. Cleaved caspase 3 was not detected in either Ad-GFP or Ad-63E transduced RPE cells (FIG. 7I). To further determine if expression of exogenous active Rap1a would induce cell death, TUNEL staining was performed in RPE 48 hours after viral transduction. As shown in FIGS. 7J and K, Ad-63E transduction did not increase TUNEL positive cells compared to Ad-GFP. Taken together, the data shown in FIG. 7 provide further support that the expression of exogenous active Rap1a reduces inflammation and VEGF without increasing cell death and autophagy.

2. Discussion

AMD is a complex and multifactorial disease characterized by irreversible central vision impairment. Although the pathophysiologic steps of AMD are still being elucidated, extensive evidence supports the concept that the progression of AMD is affected by interactions of aging, genetic and environmental factors. These interactions trigger signaling pathways involving inflammation, oxidative stress, cell death mechanisms and angiogenesis in the RPE and choroidal endothelial cells and lead to vision loss from cell degeneration and CNV. Treatments targeting vascular endothelial growth factor (VEGF) have greatly improved clinical outcomes in neovascular AMD; however, vision improvement only occurs in less than half of patients treated for neovascular AMD, and treatments remain inadequate for atrophic AMD.

Gene therapy has been gaining much attention in treating AMD as it provides the potential for long-term treatment, which would reduce the number of repeated treatments associated with local delivery with intravitreal injections of anti-VEGF agents. Gene therapy also offers possibilities to target particular cells by using cell specific promoters. Using a gene therapy approach, it was previously reported that the expression of exogenous active Rap1a in the RPE by a sc-AAV2-RPE65 vector significantly reduced laser-induced CNV in Rap1b deficient mice but not in wild type mice. In this study, another specific promoter of the RPE, VMD2, was tested in driving expression of active Rap1a in RPE in wild type mice, and the effects were compared with the sc-AAV2-RPE65. The study showed that the sc-AAV2-VMD2 vector efficiently drove active Rap1a expression in the RPE of wild type mice and transduction of sc-AAV2-VMD2 had greater specificity in the RPE compared to sc-AAV2-RPE65. The sc-AAV2-RPE65 promoter did not increase active Rap1a in RPE in wild type mice. sc-AAV2-VMD2-CARap1a treated mice with increased active Rap1a in the RPE had a significant reduction in CNV compared to those treated with the control vector sc-AAV2-VMD2-GFP. The findings from this study support the hypothesis that VMD2 has a stronger activity in driving active Rap1a expression in the RPE and increased active Rap1a is able to reduce CNV in wild type mice.

The crosstalk and feed-back loops involving inflammation, oxidative signaling and angiogenesis are implicated in the pathogenesis of AMD. The role of inflammation in experimental CNV was previously tested using the inflammatory cytokine, TNFα, as an example of a cytokine that has been associated with AMD and CNV. We reported that intravitreal TNFα contributed to experimental CNV through a mechanism involving reactive oxygen-triggered VEGF production in the RPE. Furthermore, activation of Rap1a in the RPE reduced the generation of reactive oxygen species. Here, the study showed that sc-AAV2-VMD2-CARap1a treated eyes had a significant reduction in VEGF and NF-κB phosphorylation in RPE/choroid tissues compared to control sc-AAV2-VMD2-GFP. These findings were further supported using cultured human RPE, in which increased active Rap1a by adenoviral transduction significantly reduced VEGF and p-NF-κB. However, similar effects were not observed in sc-AAV2-RPE65-CARap1a treated eyes. These results support the hypothesis that increased active Rap1a in RPE reduced CNV by reducing VEGF. The reduction in inflammatory signaling can reduce stimuli contributing to CNV, as found previously using TNFα as an inflammatory cytokine, but may also reduce atrophic AMD by interfering with processes leading to cell death.

One concern with introducing a protein to be protective is the risk of overwhelming the cell's natural abilities to manage proteins. Autophagy is one of the mechanisms by which cells deal with stresses to maintain cellular homeostasis. Through autophagy, misfolded or aggregated proteins and damaged cellular organelles that form in response to overwhelmed cellular stresses can be degraded. Therefore, increased autophagy can indirectly reflect increased cellular stresses. To determine if introduction of active Rap1a through gene therapy would cause cellular stress to trigger cell death by apoptosis or excessive activation of autophagy, the expression of cleaved caspase-3 was evaluated as a marker of apoptosis and LC3A/B as a marker of autophagy following induced expression of exogenous active Rap1a in RPE by sc-AAV2-VMD2. Compared to sc-AAV2-VMD2-GFP, sc-AAV2-VMD2-CARap1a did not increase cleaved caspase-3 but reduced caspase 3 and LC3A/B in RPE/choroid tissues in wild type mice when tested in the laser-induced CNV model. Increased active Rap1a in human RPE cells in vitro reduced LC3A/B without increasing caspase 3 activation and cell death determined by TUNEL staining.

In conclusion, the VMD2 promoter targeted RPE more specifically and increased Rap1 expression compared to the RPE65 promoter. Increased active Rap1a in the RPE by VMD2 promoter reduced three effectors associated with advanced AMD: VEGF, activated NF-κB and LC3A/B. Activation of Rap1a can protect against AMD-related stimuli leading to inflammation and angiogenesis and maintain RPE integrity and function. sc-AAV2-VMD2 vector can be an efficient and safe tool to deliver genetic materials to the RPE.

3. Materials and Methods

Animals. Five-week-old wild-type C57BL/6J (male and female) mice were purchased from the Jackson Laboratory (Bar Harbor, ME). All animal procedures were performed in accordance with the University of Utah guidelines (Guide for the Care and Use of Laboratory Animals) and the Association for Research in Vision and Ophthalmology Statement for the Use of Animals in Ophthalmic and Vision Research. All the experimental protocols were approved by IACUC and the Institutional Biosafety Committee of the University of Utah. Anesthesia was obtained with ketamine (100 mg/kg) and xylazine (20 mg/kg), and euthanasia was performed under anesthesia followed by cervical dislocation.

Construction of RPE65 or VMD2 promoter driven Self-complementary Adeno-associated Virus 2. The self-complementary adeno-associated virus 2 (sc-AAV2) vector driven by the murine RPE65 promoter was generated by the University of North Carolina Vector Core (Chapel Hill, NC)

as described previously. Briefly, the CMV promoter in the sc-AAV2 vector was replaced with a murine RPE65 promotor (1507 bp) (kindly provided by T. Michael Redmond), and synthetic sequences for the constitutively active human Rapt a Q63E mutant (CARap1a) were cloned into the scAAV2 vector with the RPE65 promoter (scAAV2-RPE65-CARap1a-GFP). The sc-AAV2 construct without CARap1a sequences was used as a control vector (scAAV2-RPE65-GFP). To compare the transduction efficiency and specificity of the RPE65 and VMD2 promoters, sc-AAV2 vectors driven by the murine VMD2 promoter (624 bp) were generated by the University of Florida-Powell Gene Therapy Center (Gainesville, FL). The sequences of CARap1a were cloned into the sc-AAV2-VMD2 as sc-AAV2-VMD2-CARap1a-GFP, and the sc-AAV2-VMD2-GFP vector was used as a control. Viruses were produced, purified and titered at the FL Powell Gene Therapy Center.

Subretinal Injections, Micron IV Imaging and Laser-induced CNV model. One microliter of sc-AAV2 (diluted in fluorescein and PBS to $5\times10^8$ viral particles) was injected into the subretinal space of each eye of 6-week-old mice. The sc-AAV2 viral transduction was monitored by in vivo live imaging using the Micron IV retinal imaging system (Phoenix Research Laboratories, Inc., Pleasanton, CA) as described previously.

Five weeks after sc-AAV2 viral injection, 11-week-old mice received laser to induce CNV. Both eyes of each mouse were dilated with one drop of 1% tropicamide ophthalmic solution. After dilation, mice were anesthetized and treated with 4 spots of 532 nm laser photocoagulation each about 2 disc diameters from the optic nerve using the Phoenix Image-Guided Laser System 94 (Phoenix Micron IV, Pleasanton, CA) at settings of ~460 mW intensity and 100 ms duration. Adequate treatment was assessed by the production of cavitation bubbles that confirmed the disruption of Bruch's membrane.[7] Seven days after laser treatment, mice were euthanized, and eyes were collected for the analysis of CNV volume and protein analysis.

Preparation of retinal pigment epithelium (RPE)/Choroid flat mounts and Analysis of CNV lesion volume. Eyes were fixed in 4% paraformaldehyde (Electron Microscopy Sciences, Hatfield, PA) for 1 hours. After removal of the cornea, lens, the vitreous and the retina, posterior eyecups of the RPE/choroid/sclera were fixed in 4% paraformaldehyde for additional 1 hour. After three washes in PBS, eyecups were blocked in PBS with 1% bovine serum albumin (BSA) and 0.5% TritonX-100 for 30 mins at room temperature and then incubated overnight at 4° C. with AlexaFluor 568-conjugated Isolectin B4 (1:200, Invitrogen, Carlsbad, CA) to label invading choroidal vessels and anti-GFP antibody to label GFP in RPE (1:500, ABCAM, Cambridge, MA). After staining, the eyecup was flattened by cutting radial incisions and flatmounted onto a microscope slide with vectashield mounting medium (Vector Laboratories, Burlingame, CA) for confocal imaging. Flatmounts were imaged by taking optical Z-sections at 3 μm increments using a confocal microscope (FV1000, Olympus, Japan), and CNV lesion volume was measured using Imaris Image Analysis Software (Bitplane USA, Concord, MA). Lesions with obvious hemorrhage or bridging CNV were excluded.

Immunostaining in Retinal Cryosections. After euthanasia, eyes were enucleated and fixed in 4% paraformaldehyde (Electron Microscopy Sciences, Hatfield, PA) for 1 hour. After removal of the cornea and lens, eyecups were incubated with 10% sucrose for two hours followed by 30% sucrose overnight at 4° C. and then embedded in optimal cutting temperature (OCT) (Tissue Tek, Hatfield, PA) and sectioned. For immunofluorescence, cryosections (12 μm) were incubated with rabbit anti-GFP (1:200) and RPE65 (1:100) from Abcam (Cambridge, United Kingdom) overnight at 4° C. after incubation in 5% normal goat serum in PBS/0.1% TritonX-100 for 1 hour to block nonspecific binding of the primary antibody. After three washes in PBS, sections were incubated for 1 hour with FITC conjugated goat anti-rabbit secondary antibody (1:200) for GFP and AlexaFluor 594-conjugated goat anti-mouse secondary antibody for RPE65 (Invitrogen, Carlsbad, CA). TO-PRO-3 (1:500, Thermo Fisher Scientific, Waltham, MA) was used to stain nuclei. The sections were mounted in Fluoromount-G (SouthernBiotech, Birmingham AL) after wash in PBS. Images were captured with an inverted microscope (OLYMPUS 1X81: Japan) at 20× magnification.

Cell culture and adenovirus transduction. Human primary RPE (hRPE; Lonza, Walkersville, MD) was grown in retinal pigment epithelial cell basal media (RtEBM, Lonza) and used from passages 4-6. The cells were transduced with adenoviral constructs expressing green fluorescent protein (Ad-GFP) or GFP-tagged active Rap1a (Ad-63E), kind gifts from Keith Burridge (University of North Carolina, Chapel Hill, NC). Forty-eight hours after viral transduction, cells were incubated with recombinant TNF-α (10 ng/ml, R&D Systems, Minneapolis, MN) or PBS for 24 hours.

TUNEL assay in cultured cells. TUNEL assays were performed per the manufacturer's instructions (In Situ Cell Death Kit, TMR red; Roche Diagnostics, Indianapolis, IN). Human RPE was plated on cell culture coverslips (Thermoscientific, Rochester, NY). After treatment, the cells were first fixed in 4% paraformaldehyde for 1 hour at room temperature. After three washes in PBS, cells were incubated with freshly prepared permeabilization solution (0.1% Triton X-100 in 0.1% sodium citrate) for 2 mins on ice. After permeabilization, some cells were incubated with DNase I (3000 U/ml in 50 mM Tris-HCl, pH 7.5, 1 mg/ml BSA) for 10 minutes at 15-25° C. as positive controls. Cells incubated only with Label Solution without Enzyme Solution were used as negative controls. To identify TUNEL+ cells, cells were incubated with TUNEL reaction mixture (Label Solution and Enzyme Solution Mix in 10:1) for 60 mins at 37° C. in a humidified incubator in the dark. After two washes in PBS, cover slips were mounted with DAPI Fluoromount G. Images were taken using a fluorescence microscope with five random images per coverslip. TUNEL+ cells determined by colabeling with DAPI stained nuclei were quantified, and the mean of TUNEL+ cells in the five images from the same coverslip was used for comparison. There were 5-6 coverslips per condition.

Protein preparation and Western blots. Protein lysates were extracted from RPE/choroid tissues as described previously.[7] Briefly, RPE/choroid tissues were homogenized in radio immunoprecipitation assay buffer (RIPA) (20 mM Tris pH 7.4, 120 mM NaCl, 0.5% sodium deoxycholic acid, 1% Triton X-100, 0.1% SDS, 10% glycerol) with protease inhibitor cocktail (Roche Diagnostics, Indianapolis, IN) and phosphatase inhibitor orthovanadate (2 mM, Sigma-Aldrich, St. Louis, MO) on ice for 20 mins. Protein lysates were collected by centrifuging at 13,000 rpm for 5 minutes at 4° C. Protein concentration in the supernatant was quantified by bicinchoninic acid assay (BCA) (Pierce, Rockford, IL). Twenty μg of protein from RPE/choroid tissues was loaded into 4% to 12% NuPAGE Bis-Tris gels (Invitrogen, Carlsbad, CA) and transferred to a PVDF membrane (Invitrogen), and then incubated with antibody to Rap1 (1:1000, BD Biosciences, San Jose, CA), VEGF (1:500, Santa Cruz Biotechnology, Santa Cruz, CA), caspase 3, LC3A/B, or phosphorylated NF-κB (1:1000, Cell signaling Technology Inc., Danvers, MA) overnight at 4° C. Membranes were reprobed with HRP-conjugated β-actin (Santa Cruz Biotechnology) as loading controls.

Densitometry was analyzed with the use of the software UN-SCAN-IT version 7.1 (Silk Scientific, Orem, UT).

Statistical analysis. Analysis of variance (ANOVA) was used to analyze protein expression and TUNEL positive cells to compare experimental and control groups, with one observation per animal or one well of cells from each treatment. Ordinary ANOVA requires that all data points, or observations, be independent, which is the case if only one observation is used per animal. When multiple observations are used per animal, and assumption is usually violated, since observations within the same animal tend to be more alike than they are between animals. The intraclass correlation coefficient (ICC) can be used to determine how correlated the observations are. If the ICC equals zero, then ordinary ANOVA provides a correct analysis. If ICC>0, however, a method such as mixed effects linear regression is required. This method is basically an ANOVA with an adjustment to the standard error to account for the lack of independence of the observations. For the CNV lesion outcome, we used mixed effects linear regression to account for lack of independence due to spots being clustered, or nested, with the same eye, with one eye per animal.

Results were displayed as Means±SEM. A P value of ≤0.05 was considered statistically significant. For animal studies, at least 40 spots from 12 individual mice were analyzed for CNV volume. Retinal sections for GFP staining and western blots of Rap1 protein were taken from 3-6 different mice.

Those skilled in the art will recognize, or be able to ascertain using no more than routine experimentation, many equivalents to the specific embodiments of the method and compositions described herein. Such equivalents are intended to be encompassed by the following claims.

REFERENCES

1 Blasiak, J., Petrovski, G., Vereb, Z., Facsko, A. & Kaarniranta, K. Oxidative stress, hypoxia, and autophagy in the neovascular processes of age-related macular degeneration. *Biomed Res Int* 2014, 768026, doi:10.1155/2014/768026 (2014).

2 Wang, H. & Hartnett, M. E. Regulation of signaling events involved in the pathophysiology of neovascular AMD. *Molecular vision* 22, 189-202 (2016).

3 Bhutto, I. & Lutty, G. Understanding age-related macular degeneration (AMD): relationships between the photoreceptor/retinal pigment epithelium/Bruch's membrane/choriocapillaris complex. *Mol Aspects Med* 33, 295-317, doi:10.1016/j.mam.2012.04.005 (2012).

4 Sparrow, J. R., Ueda, K. & Zhou, J. Complement dysregulation in AMD: RPE-Bruch's membrane-choroid. *Mol Aspects Med* 33, 436-445, doi:10.1016/j.mam.2012.03.007 (2012).

5 Ford, K. M., Saint-Geniez, M., Walshe, T., Zahr, A. & D'Amore, P. A. Expression and Role of VEGF in the Adult Retinal Pigment Epithelium. *Investigative ophthalmology & visual science* 52, 9478-9487 (2011).

6 Ablonczy, Z., Dahrouj, M. & Marneros, A. G. Progressive dysfunction of the retinal pigment epithelium and retina due to increased VEGF-A levels. *FASEB J, doi:*10.1096/fj.13-248021 (2014).

7 Wang, H. et al. Retinal pigment epithelial cell expression of active Rap1a by scAAV2 inhibits choroidal neovascularization. *Mol Ther Methods Clin Dev* 3, 16056, doi:10.1038/mtm.2016.56 (2016).

8 Wittchen, E. S. et al. Rap1 GTPase Activation and Barrier Enhancement in RPE Inhibits Choroidal Neovascularization In Vivo. *PloS one* 8, e73070, doi:10.1371/journal.pone.0073070 (2013).

9 Naso, M. F., Tomkowicz, B., Perry, W. L., 3rd & Strohl, W. R. Adeno-Associated Virus (AAV) as a Vector for Gene Therapy. *BioDrugs: clinical immunotherapeutics, biopharmaceuticals and gene therapy* 31, 317-334, doi:10.1007/s40259-017-0234-5 (2017).

10 Laredj, L. N. & Beard, P. Adeno-Associated Virus Activates an Innate Immune Response in Normal Human Cells but Not in Osteosarcoma Cells. *Journal of Virology* 85, 13133-13143, doi:10.1128/jvi.05407-11 (2011).

11 Mingozzi, F. & High, K. A. Immune responses to AAV vectors: overcoming barriers to successful gene therapy. *Blood* 122, 23-36, doi:10.1182/blood-2013-01-306647 (2013).

12 He, L., Marioutina, M., Dunaief, J. L. & Marneros, A. G. Age- and gene-dosage-dependent cre-induced abnormalities in the retinal pigment epithelium. *Am J Pathol* 184, 1660-1667, doi:10.1016/j.ajpath.2014.02.007 (2014).

13 Moshfegh, Y. et al. BESTROPHIN1 mutations cause defective chloride conductance in patient stem cell-derived RPE. *Human molecular genetics* 25, 2672-2680, doi:10.1093/hmg/ddw126 (2016).

14 Wang, H., Fotheringham, L., Wittchen, E. S. & Hartnett, M. E. Rap1 GTPase Inhibits Tumor Necrosis Factor-alpha-Induced Choroidal Endothelial Migration via NADPH Oxidase- and NF-kappaB-Dependent Activation of Rac1. *Am J Pathol* 185, 3316-3325, doi:10.1016/j.ajpath.2015.08.017 (2015).

15 Fritsche, L. G. et al. Age-related macular degeneration: genetics and biology coming together. *Annu Rev Genomics Hum Genet* 15, 151-171, doi:10.1146/annurev-genom-090413-025610 (2014).

16 Lancon, A., Frazzi, R. & Latruffe, N. Anti-Oxidant, Anti-Inflammatory and Anti-Angiogenic Properties of Resveratrol in Ocular Diseases. *Molecules* 21, 304, doi:10.3390/molecules21030304 (2016).

17 Telander, D. G. Inflammation and age-related macular degeneration (AMD). *Semin Ophthalmol* 26, 192-197, doi:10.3109/08820538.2011.570849 (2011).

18 Sobrin, L. & Seddon, J. M. Nature and nurture—genes and environment—predict onset and progression of macular degeneration. *Prog Retin Eye Res* 40, 1-15, doi:10.1016/j.preteyeres.2013.12.004 (2014).

19 Ehlken, C. et al. Switch of anti-VEGF agents is an option for nonresponders in the treatment of AMD. *Eye* (*London, England*) 28, 538-545, doi:10.1038/eye.2014.64 (2014).

20 Veloso, C. E., de Almeida, L. N., Recchia, F. M., Pelayes, D. & Nehemy, M. B. VEGF gene polymorphism and response to intravitreal ranibizumab in neovascular age-related macular degeneration. *Ophthalmic Res* 51, 1-8, doi:10.1159/000354328 (2014).

21 Theodossiadis, P. G., Liarakos, V. S., Sfikakis, P. P., Vergados, I. A. & Theodossiadis, G. P. Intravitreal administration of the anti-tumor necrosis factor agent infliximab for neovascular age-related macular degeneration. *American journal of ophthalmology* 147, 825-830, 830 e821, doi:10.1016/j.ajo.2008.12.004 (2009).

22 Markomichelakis, N. N., Theodossiadis, P. G. & Sfikakis, P. P. Regression of neovascular age-related macular degeneration following infliximab therapy. *American journal of ophthalmology* 139, 537-540, doi:10.1016/j.ajo.2004.09.058 (2005).

23 Wang, H., Han, X., Wittchen, E. S. & Hartnett, M. E. TNF-alpha mediates choroidal neovascularization by upregulating VEGF expression in RPE through ROS-dependent beta-catenin activation. *Molecular vision* 22, 116-128 (2016).

24 Wang, H. et al. Activation of Rap1 inhibits NADPH oxidase-dependent ROS generation in retinal pigment epithelium and reduces choroidal neovascularization. *FASEB J, doi:*10.1096/fj.13-240028 (2013).

25 Ahmed, C. M. et al. Repurposing an orally available drug for the treatment of geographic atrophy. *Molecular vision* 22, 294-310 (2016).

26 Sennlaub, F. et al. CCR2<sup>+</sup> monocytes infiltrate atrophic lesions in age-related macular disease and mediate photoreceptor degeneration in experimental subretinal inflammation in <em>Cx3cr1</em> deficient mice. *EMBO Molecular Medicine* 5, 1775-1793, doi:10.1002/emmm.201302692 (2013).

27 Ardeljan, D. & Chan, C. C. Aging is not a disease: distinguishing age-related macular degeneration from aging. *Prog Retin Eye Res* 37, 68-89, doi:10.1016/j.preteyeres.2013.07.003 (2013).

28 Oslowski, C. M. & Urano, F. Measuring ER stress and the unfolded protein response using mammalian tissue culture system. *Methods in enzymology* 490, 71-92, doi:10.1016/B978-0-12-385114-7.00004-0 (2011).

29 Keeling, E., Lotery, A. J., Tumbarello, D. A. & Ratnayaka, J. A. Impaired Cargo Clearance in the Retinal Pigment Epithelium (RPE) Underlies Irreversible Blinding Diseases. *Cells* 7, doi:10.3390/cells7020016 (2018).

30 Karakosta, A. et al. Choice of analytic approach for eye-specific outcomes: one eye or two? *American journal of ophthalmology* 153, 571-579.e571, doi:10.1016/j.ajo.2011.08.032 (2012).

31 Murdoch, I. E., Morris, S. S. & Cousens, S. N. People and eyes: statistical approaches in ophthalmology. *The British journal of ophthalmology* 82, 971-973, doi:10.1136/bjo.82.8.971 (1998).

We claim:

1. A nucleic acid construct comprising a nucleic acid sequence encoding a human vitelliform macular dystrophy-2 (VMD2) promoter operably linked to a nucleic acid sequence encoding active Rap1a, wherein the nucleic acid sequence encoding active Rap1a is a constitutively active Rap1a (CARap1a), wherein the CARap1a comprises the sequence of SEQ ID NO:2, wherein the human VMD2 promoter comprises the sequence of SEQ ID NO: 1.

2. The nucleic acid construct of claim 1, further comprising a selectable marker.

3. The nucleic acid construct of claim 2, wherein the selectable marker is operably linked to the vitelliform macular dystrophy-2 (VMD2) promoter.

4. A vector comprising the nucleic acid construct of claim 1.

5. A composition comprising the nucleic acid construct of claim 1.

6. The composition of claim 5, further comprising a pharmaceutically acceptable carrier.

7. The vector of claim 4, wherein the vector is a viral vector.

8. The composition of claim 5, further comprising a pharmaceutically acceptable carrier.

9. A recombinant cell comprising the nucleic acid construct of claim 1.

10. A method of treating a subject having age-related macular degeneration comprising administering an AAV vector that comprises the nucleic acid construct of claim 1 by subretinal injection to a subject in need thereof.

11. A method of inhibiting choroidal neovascularization (CNV) comprising administering an AAV vector that comprises the nucleic acid construct of claim 1 by subretinal injection to a subject in need thereof.

12. A method of reducing choroidal neovascularization (CNV) comprising administering to a subject an AAV vector that comprises the nucleic acid construct of claim 1 by subretinal injection to a subject in need thereof.

13. A method of reducing inflammatory signaling in choroid tissue comprising administering to a subject an AAV vector that comprises the nucleic acid construct of claim 1 by subretinal injection to a subject in need thereof.

14. A method of reducing VEGF expression in choroid tissue comprising administering to a subject an AAV vector that comprises the nucleic acid construct of claim 1 by subretinal injection to a subject in need thereof.

* * * * *